United States Patent [19]

Lerch et al.

[11] Patent Number: 5,321,139
[45] Date of Patent: Jun. 14, 1994

[54] PROCESS FOR THE ENANTIOSELECTIVE SYNTHESIS OF 2(R)-BENZYLSUCCINIC ACID MONOAMIDE DERIVATIVES

[75] Inventors: Ulrich Lerch, Hofheim am Taunus; Heiner Jendralla, Frankfurt am Main; Bernhard Seuring, Hofheim am Taunus; Rainer Henning, Hattersheim am Main, all of Fed. Rep. of Germany

[73] Assignee: Hoechst Aktiengesellschaft, Frankfurt am Main, Fed. Rep. of Germany

[21] Appl. No.: 22,887

[22] Filed: Feb. 16, 1993

Related U.S. Application Data

[62] Division of Ser. No. 876,331, Apr. 30, 1992, abandoned.

[30] Foreign Application Priority Data

May 3, 1991 [DE] Fed. Rep. of Germany ....... 4114401

[51] Int. Cl.$^5$ .................. C07D 211/06; C07C 231/02
[52] U.S. Cl. .................................. 546/224; 556/136;
560/41; 560/43; 585/269; 502/162; 502/166;
502/167; 546/216; 546/238; 544/172; 544/355;
544/386; 540/575; 548/334.1; 548/374.1;
548/540
[58] Field of Search ...................... 546/224, 216, 238;
560/41, 43; 585/269; 556/136; 502/162, 166,
167; 544/172, 335, 386; 540/575; 548/334.1,
374.1, 540

[56] References Cited

FOREIGN PATENT DOCUMENTS

| 2456937 | 6/1975 | Fed. Rep. of Germany . |
| 253947A1 | 2/1988 | Fed. Rep. of Germany . |
| 4028741A1 | 3/1991 | Fed. Rep. of Germany ......... C07D 401/14 |
| 02157243 | 6/1990 | Japan . |

OTHER PUBLICATIONS

Ito et al.; Tet. Lett. 31(19) 2731; 1990.
Chemical Abstracts, vol. 114, No. 1, Jan. 7, 1991, Columbus, Ohio; abstract no. 7252q, A. Terajima et al., "Preparation of (R)-2-(1-naphthylmethyl)succinic acid as an intermediate for renin-inhibitory peptides," p. 716.
Chemical Abstracts, vol. 114, No. 5, Feb. 4, 1991, Columbus, Ohio; abstract no. 43168a, K. Achinami et al., "Preparation of asymetric trans-4,5-bis[4-methoxy-3,-5-dimethylphenyl)phosphinomethyl]-2,2-dimet," p. 780.

(List continued on next page.)

Primary Examiner—Marianne M. Cintins
Assistant Examiner—Michael B. Hydorn
Attorney, Agent, or Firm—Finnegan, Henderson, Farabow, Garrett & Dunner

[57] ABSTRACT

Two processes are described for the preparation of the optically pure compounds of formula 1:

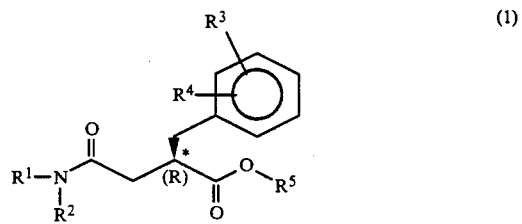

in which $R^1$ and $R^2$ are e.g. alkyl, $R^3$ and $R^4$ are e.g. hydrogen and $R^5$ is e.g. hydrogen. Both processes include, as key steps, the enantioselective hydrogenation of a C=C double bond and the regioselective formation of a dicarboxylic acid monoamide derivative. In one process a phenylitaconic acid derivative is asymmetrically hydrogenated to give an optically active (R)-benzylsuccinic acid which is then converted to a diester, said diester being converted to the monoamide compound of formula 1. In the second process, a phenylitaconic acid derivative is converted to its anhydride, and the anhydride is then converted to a monoamide which is then asymmetrically hydrogenated to give the compound of formula 1.

7 Claims, No Drawings

FOREIGN PATENT DOCUMENTS

Chemical Abstracts, vol. 113, No. 7, Aug. 13, 1990, Columbus, Ohio; abstract no. 59204z, K. Achinami et al., "Preparation of optically-active 2-1(1-naphthylmethyl)succinic acid or its monoamide with piperidine, morpholine or dialkylamine", p. 708.

Kawano et al., "Ruthenium(II)-BINAP Complex Catalyzed Asymmetric Hydrogenation of Unsaturated Dicarboxylic Acids", Tetrahedron Letters, vol. 28, No. 17, (1987) pp. 1905–1908.

J. J. Plattner et al., J. Med. Chem. vol. 31, 2277 (1988).

W. S. Johnson et al., Organic Reactions vol. 6, pp. 1–73 (1951).

E. C. Horning et al., J. Am. Chem. Soc., vol. 74, 5147 (1952).

A. M. El-Abbady et al., J. Org. Chem., vol. 26, 4871 (1961).

L. S. El-Assal et al., J. Chem. Soc. 2983, (1963).

K. R. Rao et al., Indian, J. Chem., vol. 7, 859 (1969).

J. Andersson et al., NOUV., J. Chim., vol. 1, 413 (1977).

T. Momose et al., Chem. Pharm. Bull., vol. 25, 2755 (1977).

A. Maercker, Org. React., 14, 270–490, (1965).

R. F. Heck, Palladium Reagents in Organic Synthesis, Academic Press, New York, 1985, [Detailed Contents].

T. Harada et al., Chem. Lett., 1195, (1978).

A. Tai et al., Chem. Lett. 2083 (1984).

W. Vocke et al., Chem. Techn., 39, 123 (1987).

H. Brunner et al., J. Organomet, Chem., 387, 209 (1990).

K. E. Keonig in "Asymmetric Synthesis" vol. 5, pp. 71–91, ed. Morrison, J. D. Academic Press, Orlando (1985).

J. W. ApSimon et al., Tetrahedron Report Number 209, vol. 42, 5157 (1986).

H. Brunner, Top, Stereochem., 18, 129 (1988).

I. Olima et al., Tetrahedron Report Number 264, vol. 45, 6901 (1989).

H. Brunner et al., J. Organomet. Chem., 384, 223 (1990).

W. C. Christopfel, et al., J. Am. Chem. Soc. 101, 4406 (1979).

H. Pielartzik et al. B. Irmisch-Pielartzik and T. Eicher, "Houben–Weyl", (Methods of Organic Chemistry, vol. E5 (Carboxylic Acids and Carboxylic Acid Derivatives), ed. J. Falbe, pp. 633–652; Carbonsaureanhydridi (Carboxylic Acid Anhydrides, G.) Thieme Verlag, Stuggart (1985).

H. Brunner et al., Synthesis, 743 (1989).

K. Mashima et al., J. Chem. Soc., Chem Commun. 1208 (1989).

G. L. Baker et al., J. Org. Chem. 46, 2954 (1981).

I. Ojima et al., Tetrahedron Lett., 21, 1051 (1980).

T. Ohta et al., Inorg. Chem., 27, 566 (1988).

M. T. Ashley et al., J. Am. Chem. Soc., 113, 589 (1991).

H. Kawano et al., J. Chem. Soc. Perkin Trans. I., 1571 (1989).

PROCESS FOR THE ENANTIOSELECTIVE SYNTHESIS OF 2(R)-BENZYLSUCCINIC ACID MONOAMIDE DERIVATIVES

This application is a division of application Ser. No. 07/876,331 filed Apr. 30, 1992, now abandoned.

The compounds of formula (1) are valuable intermediates for the synthesis of pharmaceutical active ingredients, especially of renin-inhibiting compounds, e.g. those presented in German patent documents A-39 30 397 and A-39 33 096. The compounds described by formula (1) have hitherto been obtained—where known—by asymmetric substitution of the enolate of a homochiral 3-phenylpropionyloxazolidinone on to bromoacetic acid esters as the key step, e.g. according to J. J. Plattner et al. [J. Med. Chem., vol. 31, 2277 (1988), scheme V].

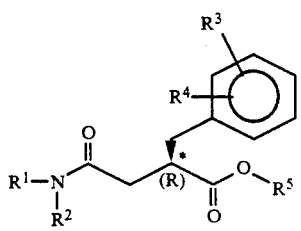
(1)

The present invention relates to a process for the preparation of specially configured, optically active compounds of formula (1), in which $R^1$ and $R^2$
a) can be identical or different and are linear or branched alkyl having 1 to 7 carbon atoms or cycloalkyl having 5 to 7 carbon atoms.
  $a_1$) The afore-mentioned alkyl and cycloalkyl groups can be substituted by one, two or three identical or different radicals selected from the group comprising
  $(C_1-C_7)$-alkyl (branched or unbranched)
  hydroxyl (protected or unprotected)
  $(C_1-C_7)$-alkoxy
  amino (protected or unprotected)
  $(C_1-C_7)$-alkylamino (protected or unprotected)
  di-$(C_1-C_7)$-alkylamino.
  $a_2$) $R^1$ and $R^2$ can be bonded together to form a 5- to 7-membered ring of which 0, 1 or 2 ring members can be identical or different and be oxygen or nitrogen atoms, it being possible for the ring to be unsubstituted or substituted by the radicals mentioned under $a_1$).
b) $R^1$ and $R^2$ can also be phenyl groups which are unsubstituted or substituted by groups having the meanings given below for $R^3$ and $R^4$.

The group $NR^1R^2$ preferably has the following meanings:
pyrrolidinyl
pyrazolidinyl
imidazolidinyl
piperidinyl
piperazinyl
tetrahydropyrimidinyl
3-hydroxypiperidinyl
4-hydroxypiperidinyl
3-aminopiperidinyl
4-aminopiperidinyl
morpholinyl
1,4-diazacycloheptyl (homopiperazinyl)
(all the hydroxyl and amino groups being protected or unprotected).

$R^3$ and $R^4$ can be identical or different and are hydrogen, trifluoromethyl, halogen or the substituents mentioned under $a_1$). $R^3$ and $R^4$ are preferably hydrogen atoms.

$R^5$ is
c) hydrogen or
d) an aromatic or aliphatic radical which is unsubstituted or substituted by electron-attracting substituents such as e.g. fluorine, chlorine, bromine, alkoxycarbonyl, aminocarbonyl, alkanoyl, aryloyl, nitro etc., preferably a substituted or unsubstituted phenyl radical.

The compound (1) is a monocarboxylic acid in case c) and an active ester of this monocarboxylic acid in case d).

Suitable protecting groups for amino groups and/or hydroxyl groups are the structures generally known to those skilled in the art.

Both process variants according to the invention are based on the asymmetric hydrogenation of an $\alpha$, $\beta$-unsaturated carboxylic acid; in principle, both processes can also be carried out on the industrial scale.

The invention further relates to compounds of formula (1) and to their use e.g. as intermediates for the preparation of active ingredients, especially of pharmaceutical agents.

In step 1 of the first process (scheme 1), an intermediate half-ester is obtained in the course of a Stobbe condensation from a succinic acid diester 2 ($R^6$ is a linear or branched alkyl radical) and a benzaldehyde 3 in the presence of a base; said half-ester can be converted by saponification to the phenylitaconic acid 4 without working-up or isolation, this step being known in the literature (W. S. Johnson, Organic Reactions, vol. 6, pages 1 to 73 (1951)). In principle, the reaction can be carried out in a large number of solvents using a variety of bases and over a wide temperature range (see 1. Johnson, op. cit.; 2. E. C. Horning, J. Am. Chem. Soc., vol. 74, 5147 (1952); 3. A. M. El-Abbady et al., J. Org. Chem., vol. 26, 4871 (1961); 4. L. S. El-Assal et al., J. Chem. Soc., 2983 (1963); 5. K. R. Rao, Indian J. Chem., vol. 7, 859 (1969); 6. J. Andersson et al., Nouv. J. Chim., vol. 1, 413 (1977); 7. T. Momose et al., Chem. Pharm. Bull., vol. 25, 2755 (1977)).

Scheme 1
Process variant 1 according to the invention

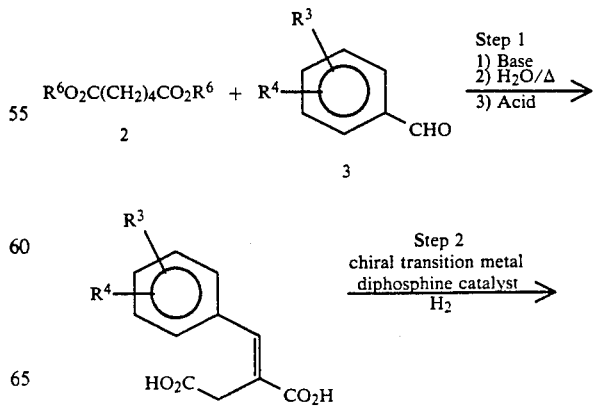

3

-continued
Scheme 1
Process variant 1 according to the invention

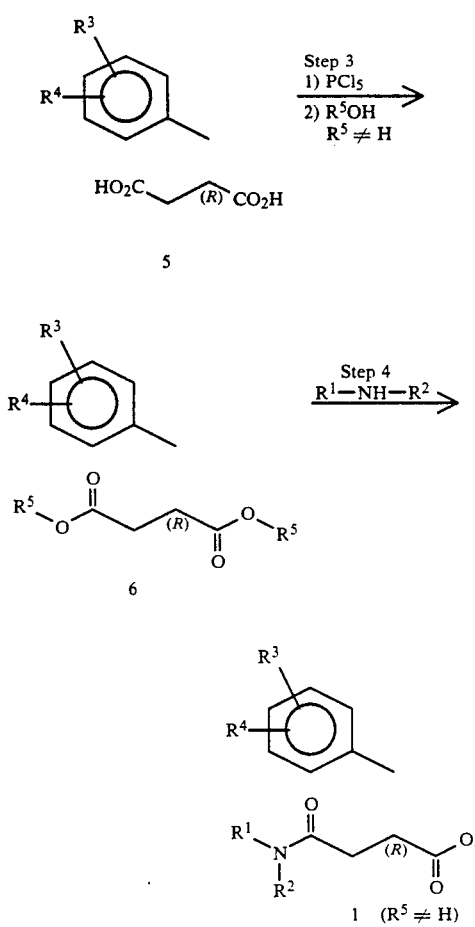

Scheme 2
Process variant 2 according to the invention

4

-continued
Scheme 2
Process variant 2 according to the invention

It is known that, alternatively, compounds of formula 4 can also be prepared by means of a Wittig reaction of a 2-triphenylphosphoranylidenesuccinic acid half-ester with the benzaldehyde 3 (A. Maercker, Org. React., 14, 270–490 (1965)), followed by saponification of the half-ester of 4. As a further alternative, it is known that compounds of formula 4 can also be obtained by means of a so-called Heck reaction (R. F. Heck, Palladium Reagents in Organic Syntheses, Academic Press, New York, 1985), where itaconic acid or its half-ester or diester is coupled with a halogenobenzene $R^3R^4$—$C_6H_3$—X (X=Cl, Br, I, preferably I) in the presence of catalytic amounts of a palladium salt, e.g. Pd(OAc)$_2$, and triphenylphosphine, if necessary in the presence of a base such as triethylamine, and, if appropriate, the half-ester or diester formed is then saponified to the dicarboxylic acid 4.

In step 2 of the first process according to the invention (scheme 1), the phenylitaconic acid 4 is asymmetrically hydrogenated to the optically active (R)-benzylsuccinic acid 5. It is known that, in principle, heterogeneous enantioselective hydrogenations with an enantiomeric excess (ee) of >90% can be achieved on Raney nickel catalysts which have been modified with tartaric acid and sodium bromide (T. Harada et al., Chem. Lett., 1195 (1978); A. Tai et al., Chem. Lett., 2083 (1984)). Because of the known allergenic potential of nickel and the poor reproducibility of the method, such heterogeneous catalysts seem rather unattractive, for example for the synthesis of drugs.

In the present patent application, the optical induction is therefore achieved using a dissolved, optically pure metal-organic complex as the hydrogenation catalyst. The relatively expensive catalyst needs to be present in the reaction mixture only at a very low concentration. The molar ratios of substrate reacted to catalyst used are generally between 100 and approx. 50,000, preferably between 100 and 5000, depending on the catalyst and substrate. The upper limit of the substrate/catalyst ratio is essentially due to the fact that the "active catalyst" present under hydrogenation conditions is normally consumed rapidly and irreversibly by oxygen. The required amount of catalyst therefore depends essentially on how thoroughly the reaction solution can be degassed before the hydrogenation begins and how completely air is excluded during the course of the hydrogenation [see e.g. W. Vocke et al., Chem. Techn., 39, 123 (1987)].

Approx. 0.1–0.5 mol % of catalyst is normally sufficient. It is preferable to use complexes in which the central atom is either a rhodium(I) cation (see 11, 13 in scheme 3) or a ruthenium(II) cation (see 16, 18, 19).

Before the hydrogenation begins, a solution of the substrate (4 or 8), the precatalyst and, if appropriate, additives (e.g. an amine) in a suitable inert solvent or solvent mixture is placed in the reaction vessel. The degassed solution is then shaken or stirred under 1 to 200 atm, preferably under 1 to 50 atm, of hydrogen gas.

Instead of using hydrogen gas, it is also possible to carry out transfer hydrogenation in the presence of a hydrogen source, e.g. formic acid/triethylamine or isopropanol. The principle of the enantioselective transfer hydrogenation of C=C double bonds has been described by H. Brunner et al. [J. Organomet. Chem., 387, 209 (1990)]. Applications of this principle to the asymmetric hydrogenation of 4 or 8 are given in the Examples of the present patent application.

The hydrogenation can be carried out in the temperature range from about $-40°$ C. to $+80°$ C., preferably at $-20°$ to $+40°$ C. and particularly preferably at $0°$ to $30°$ C., depending on the substrate and catalyst. It is supposed that the oxygen-sensitive "active catalyst" is formed by reductive cleavage of the ligands $Y^1$ (in the case of 11) or L—L (in the case of 13) and has structure 14, in which the two freed coordination sites are occupied by the substrate (e.g. the two carboxylate groups in the case of the hydrogenation of 4 in the presence of triethylamine). The extent of the hydrogenation (from 4 to 5 or from 8 to 9) can be monitored by measuring the hydrogen consumption or by HPLC analysis. The enantioselectivity of the hydrogenation of a given substrate is influenced, in some cases to a considerable degree, by parameters such as the reaction temperature, the hydrogen pressure, the nature of the solvent and the presence of additives. These effects are generally difficult to predict. For example, the enantioselectivity of some optically active rhodium(I) diphosphine complexes decreases markedly when a particular limiting hydrogen pressure is exceeded, whereas when a different type of diphosphine is present, the enantiomeric excess (ee) of the product either remains unaffected or even increases. As a rule, the hydrogenation rate increases with increasing hydrogen pressure and less catalyst is needed. A temperature rise also normally results in an acceleration of the hydrogenation, but is often associated with a lowering of the enantiomeric excess and a shortening of the life of the catalyst. In some cases, however, the optimum result is achieved by raising the temperature and shortening the hydrogenation time. As a rule, it will be possible to improve the enantioselectivity of the hydrogenation of a given substrate/catalyst pair by cooling to $-20°$ C. to $0°$ C. and allowing for a longer hydrogenation time. The influence of an additive, such as e.g. triethylamine or optically active 1-phenylethylamine, on the enantioselectivity of the asymmetric hydrogenation is difficult to calculate, but sometimes important. Whereas e.g. the hydrogenation of phenylitaconic acids 4 with the rhodium complex of BPPM (20 or 21) yields benzylsuccinic acids 5 with a high enantiomeric excess only in the presence of one equivalent of an amine, the enantioselectivity of some other substrate/catalyst pairs remains unaffected in the presence of triethylamine or even decreases substantially in a few cases.

Likewise, for a given metal ($Rh^I$ or $Ru^{II}$) and a given optically active diphosphine, it is difficult to determine the superiority or inferiority of a cationic precatalyst compared with a neutral precatalyst (see scheme 3). In the majority of cases, the cationic rhodium(I) complexes 13 have a higher catalytic activity and a greater enantioselectivity than corresponding neutral complexes 11. In some cases, however, the reverse situation applies.

In principle, suitable solvents for the asymmetric hydrogenation are any liquids which dissolve the substrate, catalyst and any additives used and which are inert under the reaction conditions. Unbranched and branched alcohols, inter alia, meet these requirements, methanol, ethanol, propanol or isopropanol being preferred because they are easily removed under vacuum. However, some catalysts exhibit an increasing enantioselectivity with decreasing solvent polarity, i.e. they give products with a higher enantiomeric excess in isopropanol than in methanol. In these cases, it is convenient to add a non-polar cosolvent miscible with the alcohol or to carry out the hydrogenation directly in a solvent of low polarity.

The preparation of the optically active precatalysts is outlined in scheme 3. Scheme 4 is a collation of some optically active bis(diarylphosphino) compounds of formula 10 which have been studied in the present patent application. Of these, the compounds 20, 24–27, 29 and 33 are commercially available; the compounds 21 (G. L. Baker et al., J. Org. Chem., 46, 2954 (1981)), 22 (I. Ojima et al., Tetrahedron Lett., 21, 1051 (1980)) and 28 (H. W. Krause et al., East German patent document A-253 947) were prepared by literature methods. The compounds 23, 30, 31 and 32 have not been previously described and their preparation is described in the Examples of the present patent application. There are some other chiral diphosphines of formula 10 which are commercially available and a large number which are known in the literature. The present invention includes the use of all these diphosphines 10 and other diphosphines of formula 10 within the framework of the process described here for the preparation of compounds of formula 1.

A survey of known chiral diphosphines of formula 10 and their use for the asymmetric hydrogenation of C=C double bonds can be found in:

a) K. E. Koenig in "Asymmetric Synthesis", vol. 5, ed. Morrison, J. D., Academic Press, Orlando 1985, page 71 et seq.;

b) J. W. ApSimon et al., Tetrahedron, 42, 5157 (1986), pages 5173–5186;
c) H. Brunner, Top. Stereochem., 18, 129 (1988);
d) I. Ojima et al., Tetrahedron, 45, 6901 (1989), pages 6902–6916.
Scheme 3
Chiral transition metal diphosphine complexes for carrying out the catalytic asymmetric hydrogenations of a dicarboxylic acid 4 or a monocarboxylic acid monoamide 8 (cf. schemes 1 and 2)
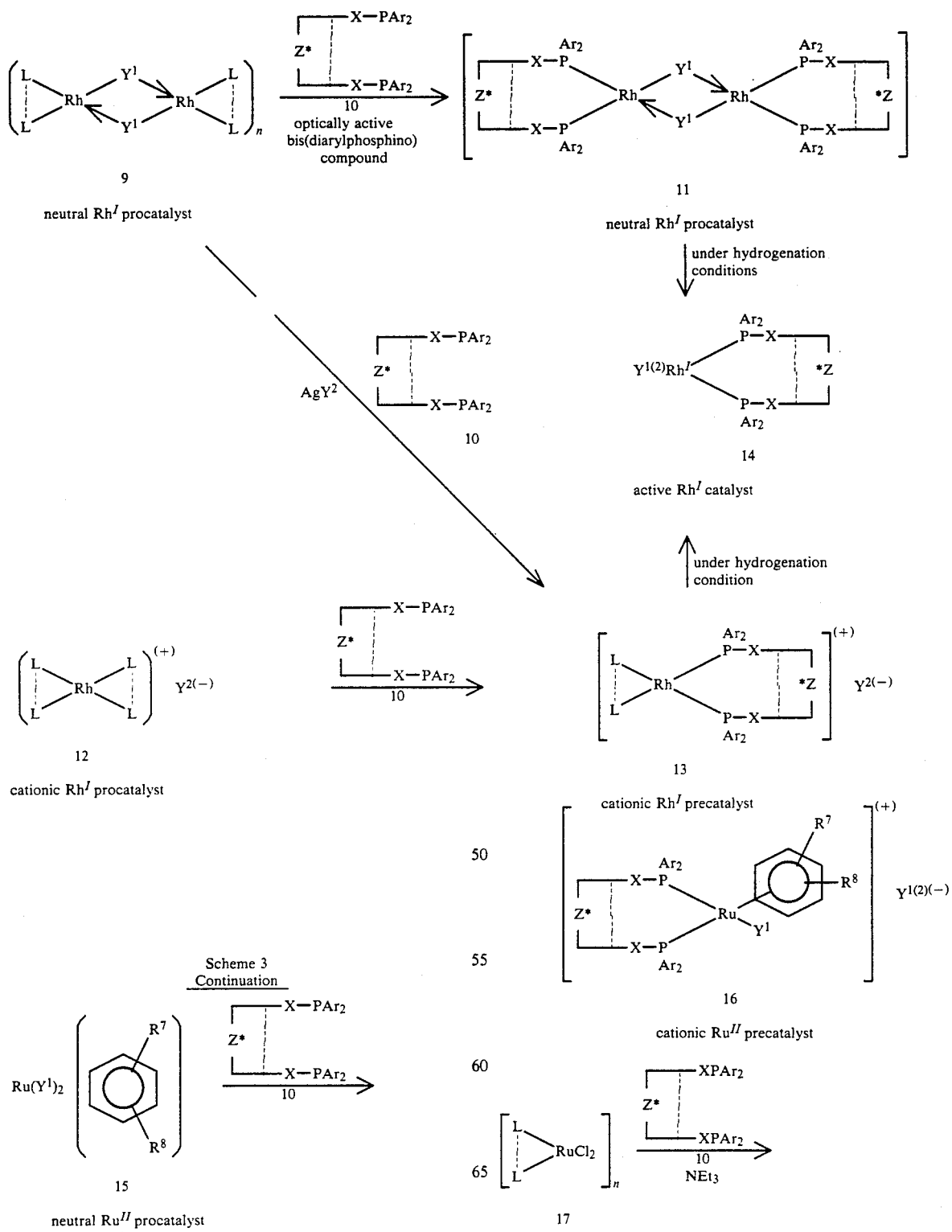

-continued
Scheme 3 Continuation

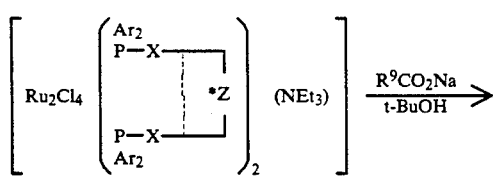

18 neutral Ru^II precatalyst

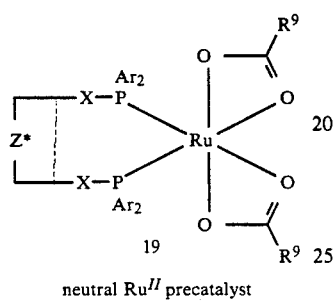

19 neutral Ru^II precatalyst

Scheme 4
Optically active bis(diarylphosphino) compounds, used in the Examples of the present invention, of the formula

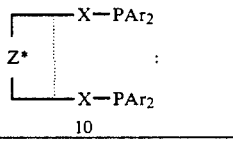

10

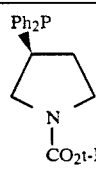 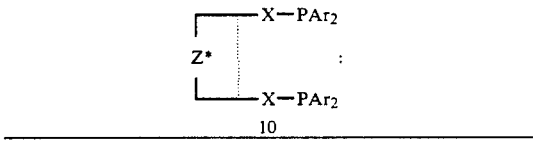

(2S,4S)(−)-BPPM    (2R,4R)(+)-BPPM
20                  21

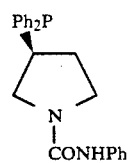 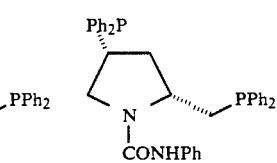

(2S,4S)(−)-Phenyl-CAPP    (2R,4R)(+)-Phenyl-CAPP
22                         23

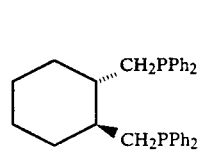

24

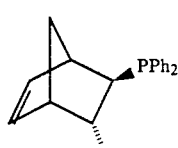

(−)-Norphos
25

-continued
Scheme 4
Optically active bis(diarylphosphino) compounds, used in the Examples of the present invention, of the formula

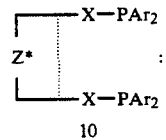

10

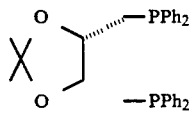

(+)-DIOP
26

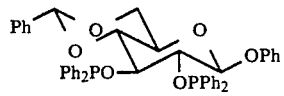

(−)-Phenyl-4,6-O-(R)benzylidene-2,3-(O)-bis(di-phenylphosphino)-β-D-glucopyranoside

Scheme 4 Continuation

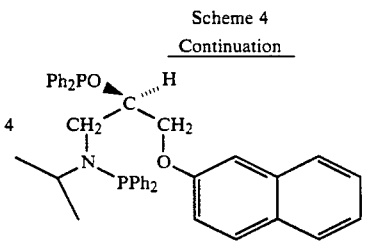

(R)(−)Propraphos
PPP
28

(2S,4S)(−)-Bis(diphenylphosphino)pentane
29

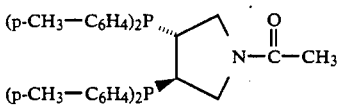

(3R,4R)(+)-1-Phenylaminocarbonyl-3,4-bis(diphenylphosphino)pyrrolidine
30

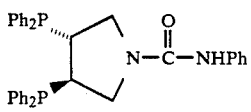

(3R,4R)(+)-1-Phenylaminocarbonyl-3,4-bis(diphenylphosphino)pyrrolidine
31

-continued
Scheme 4
Continuation

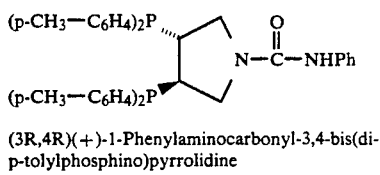

(3R,4R)(+)-1-Phenylaminocarbonyl-3,4-bis(di-p-tolylphosphino)pyrrolidine

32

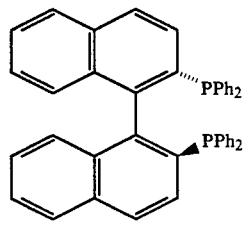

(S)(−)-BINAP

33

The indicated survey articles also show that the chiral hydrogenation catalysts can be modified in a variety of ways, e.g. immobilized by adsorption or binding (in some cases via spacers) to inorganic solids (silica gel, activated charcoal etc.) or to swellable resins (polymers) (see H. Brunner et al., J. Organomet. Chem., 384, 223 (1990)), or converted to water-soluble catalysts by means of suitable substituents of high polarity. When the reaction has ended, immobilized catalysts can be removed from the reaction mixture by filtration, which simplifies the working-up process. Furthermore, the catalysts filtered off can occasionally be re-used in subsequent hydrogenation batches (recycling) without loss of activity or enantioselectivity. The use of water-soluble catalysts makes it possible to use water as the solvent, which is harmless to the environment and inexpensive, or easily to remove the catalyst, when the hydrogenation has ended, by washing with water when a non-polar solvent is used. The present invention further relates to the use of such modified hydrogenation catalysts in asymmetric hydrogenation within the framework of the enantioselective synthesis of compounds of formula 1.

It is also found experimentally that the resolution of the racemate rac.-1 ($R^5=H$) gives a poor yield. If, on the other hand, (R)-1 ($R^5=H$) of $\geq 80\%$ ee is used, optically pure (R)-1 is obtained in almost quantitative yield with a single crystallization.

Therefore the possibility of adding such a racemate resolution step in order to increase the optical purity of compounds of formula 1 also forms part of the present process for the enantioselective synthesis of compounds of formula 1.

In scheme 3, the symbols have the following meanings: L is a monodentate (normally achiral) ligand occupying one coordination site in the coordination shell of $Rh^I$ or $Ru^{II}$. Advantageously, two of these monodentate ligands L are bonded together to form a ring. A cyclic bidentate ligand corresponds to these conditions. A preferred meaning of L—L is therefore e.g. 1,5-cyclooctadiene or 2,5-norbornadiene. $Y^1$ is chlorine, bromine or iodine, preferably chlorine. $Y^2$ is an anion which is less nucleophilic than chloride, e.g. $BF_4^-$, $SbF_4^-$, $SbF_6^-$, $PF_6^-$, $ClO_4^-$ or $CF_3SO_3^-$, preferably $BF_4^{31}$. In the active catalyst 14, the anion Y can have the meaning of either $Y^1$ or $Y^2$, depending on whether the precursor was the neutral precatalyst 11 or the cationic precatalyst 13. Likewise, the anion Y in the cationic $Ru^{II}$ complex 16 can have the meaning of either $Y^1$ or $Y^2$. $R^7$ and $R^8$ are identical or different and are hydrogen or linear or branched alkyl having 1-4 carbon atoms. $R^9$ is linear or branched alkyl or alkenyl having 1-4 carbon atoms. As can be seen from the examples in scheme 4, the optically active bis(diarylphosphino) compounds of formula 10 embrace a large number of structural types. Their chirality always has its origin in the carbon skeleton, which has been symbolized by the asterisk in the appropriate part of the molecule. Outside the structural sphere of validity of formula 10 there are diphosphines whose chirality is based exclusively on the presence of chiral phosphorus atoms, i.e. which have the formula

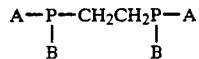

Thus, the chiral phosphorus compound DIPAMP (M. S. Knowles et al., German patent 2 456 937) and analogs thereof are not covered by the present invention. The compounds of formula 10 can have an open-chain chiral carbon skeleton (see e.g. 28, 29 and 33 in scheme 4) or a monocyclic or polycyclic chiral carbon skeleton (see e.g. 24, 25), symbolized in 10 by the broken line. The chiral carbon skeleton can include one or more heteroatoms Z, which can be nitrogen, N, or oxygen, O (see e.g. 20-23, 26, 27). The two diarylphosphino groups can be bonded to the chiral carbon skeleton via carbon atoms ($X=CH_2$) (see e.g. 26) or via heteroatoms ($X=O$ or $N$) (see e.g. 28, 27), but the diarylphosphino groups can also be bonded directly to the chiral carbon skeleton (X in these cases symbolizing a chemical bond rather than an atom; see e.g. 24, 25, 29-33).

The asymmetric hydrogenations of C═C double bonds which are known in the literature and included in the four review articles cited above are aimed substantially at hydrogenations of N-acyldehydroamino acids. These studies are irrelevant in terms of the present invention because the feasibility and enantioselectivity of asymmetric hydrogenations are known to depend to a large extent on the nature of functional groups on the substrate which are capable of coordination and their spatial arrangement relative to the double bond to be hydrogenated. Asymmetric hydrogenations of substrates which are structurally similar to formulae 4 and 8 relevant here are described e.g. by K. E. Koenig (in "Asymmetric Synthesis", vol. 5, Table 11, page 90), who collates the known asymmetric hydrogenations of itaconic acid. Itaconic acid differs from formula 4 in that it does not possess the substituent $R^3R^4C_6H_3$—. This publication states that 2(S)-methylsuccinic acid was obtainable with a good enantioselectivity by means of the commercially available chiral diphosphine (S,S)-BPPM 20. However, the (R) configuration relevant in the context of the present invention was not satisfactorily obtainable. Scarcely any experiments on asymmetric hydrogenations of itaconic acid monoamides are mentioned. Here only the hydrogenation of an itaconic acid monobenzylamide with (R,R)-DIPAMP is known (see K. E. Koenig, Table 11, page 91). The underlying original work (W. C. Christopfel, B. D. Vineyard, J. Am. Chem. Soc., 101, 4406 (1979)) does not describe the present invention because a) no work was carried out on phenylitaconic acid derivatives, b) the catalyst diphosphine DIPAMP is outside the definitions of the present invention (vide supra).

In step 3 of the first process according to the invention (scheme 1), the optically active benzylsuccinic acid is converted to a diester 6. In principle, the diester 6 can be prepared by direct esterification of the dicarboxylic acid 5 with the hydroxyl compounds $R^5OH$ or by the intermediate formation of a double acid halide. In principle, the acid halide can be prepared by means of phosphorus pentachloride, phosphorus trichloride, phosphorus oxychloride, phosphorus tribromide, thionyl chloride, oxalyl chloride or other reagents capable of producing carboxylic acid halides from carboxylic acids. The intermediate acid halide can be isolated, e.g. by distillation, or converted directly to the diester 6 without isolation.

Preferably, the intermediate preparation of the double acid chloride is carried out by means of phosphorus pentachloride in toluene at 40°–45° C., the solvent is removed under vacuum and the oily reside is reacted directly with the hydroxyl compound $R^5OH$. In principle, this method can be used to prepare diesters 6 whose radical $R^5$ is limited only by the availability of the hydroxyl compound $R^5OH$. In practice, however, the quality of the process depends decisively on the diester 6 and hence the radical $R^5$ meeting various requirements. These are:

a) The diester 6 must be stable towards racemization under the conditions of its preparation and its conversion to the monoamide 1 ($R^5 \neq H$).

b) The diester 6 must not be too highly activated because otherwise an adequate regioselectivity is not obtained in the conversion to the monoamide 1 ($R^5 \neq H$).

c) On the other hand, the diester 6 must not be too highly deactivated either, because the monoamide 1 ($R^5 \neq H$) should be capable of coupling with primary or secondary amino groups without racemization, e.g. for the preparation of renin inhibitors. Although a known method of coupling such amines and the free carboxylic acid 1 ($R^5 \neq H$) exists according to German patent document A-39 30 397, the saponification of esters of formula 1 ($R^5 = H$) to carboxylic acids of formula 1 is associated with racemization under the conventional conditions (dilute aqueous sodium hydroxide solution) (see Examples). For this reason and in order to save synthesis steps, it is necessary to obtain an ester 1 ($R^5 \neq H$) which is capable of coupling directly.

d) The hydroxyl compound $R^5OH$ should be easily obtainable or inexpensive.

e) To allow convenient purification, the diester 6 should have a high crystallization tendency.

It has been found that substituted phenyl compounds and especially the hydroxyl compound p-nitrophenol ($R^5 = O_2N-C_6H_4-$) meet the requirements a) to e) satisfactorily. For example, the reaction of the crude double acid chloride with 2.05 mol equivalents of p-nitrophenol in the presence of 2.5 mol equivalents of triethylamine at $-20°$ to 80° C., preferably at 15° to 25° C., in suitable inert solvents, under the preferred conditions, is quantitative within 8–24 hours. The bis(p-nitrophenyl) esters 6 ($R^5 = p$-$O_2NC_6H_4$) have a high crystallization tendency and can easily be precipitated from concentrated organic solution, in almost quantitative yield, by the addition of e.g. hydrocarbons or nonpolar ethers, preferably diisopropyl ether or methyl tert-butyl ether. The reprecipitated diesters 6 are chemically pure. Their optical purity is at least equivalent to that of the dicarboxylic acids 5 used. If dicarboxylic acids 5 of high optical purity ($\geq 95\%$ ee) are used as starting materials, practically optically pure diesters 6 ($R^5 = p$-$O_2N-C_6H_4-$, $>99\%$ ee) are obtained.

In step 4 of the first process according to the invention (scheme 1), the optically active (optically pure) diester 6 is reacted with the amine $R^1R^2NH$ to give the monoamide 1. In principle, the reaction can be carried out in any inert solvent and over a wide temperature range (e.g. approx. $-40°$ C. to $+100°$ C.). The reaction of the preferred bis(p-nitrophenyl) ester ($R^3$, $R^4 = H$, $R^5 = p-O_2N-C_6H_4-$) with the preferred amines $R^1R^2NH$ proceeds quantitatively in 0.5–5 hours, e.g. in DMF at $-10°$ C. to 30° C. The p-nitrophenol formed can conveniently be removed quantitatively from the organic solution of the crude product by extraction with approx. 0.5 molar sodium hydroxide solution. It precipitates out on acidification of the aqueous extracts and can be re-used for the preparation of subsequent batches of 6 from 5 (reagent recycling) after suction filtration and drying. The worked-up crude product 1 already has a high regioselectivity.

The reaction of the active ester monoamide 1, obtained according to scheme 1, with primary or secondary amines to give corresponding diamides, e.g. renin inhibitors, proceeds under mild conditions in good yield without racemization.

The preferred reaction conditions for the reaction of the monoester 1 to give the diamide are similar to the conditions for the reaction of the diester 6 to give the monoamide 1. The preferred reaction temperature of approx. 20°–70° C., especially 30°–50° C., is somewhat higher than for the reaction of the diester 6.

The second process according to the invention is outlined in scheme 2. Step 1 of this process is identical to the corresponding step of the first process according to the invention.

Step 2 of the second process according to the invention is a condensation of the unsaturated dicarboxylic acid 4 with the elimination of water and the formation of the unsaturated anhydride 7. This reaction can be carried out with a large number of water-eliminating reagents or purely by the action of heat (see e.g. T. Eicher et al. in "Houben-Weyl, Methoden der Organischen Chemie (Methods of Organic Chemistry)", vol. E5 "Carbonsäuren und Carbonsäure-Derivate (Carboxylic Acids and Carboxylic Acid Derivatives)", ed. J. Falbe, pages 633–652: "Carbonsäureanhydride (Carboxylic Acid Anhydrides)", G. Thieme Verlag, Stuttgart 1985).

The solvent and reaction temperature are not critical. It is also possible to carry out the reaction either without a solvent, in which case the water-eliminating reagent is liquid and partially dissolves the dicarboxylic acid, or as a solid-phase reaction. It is preferable to carry out the reaction at room temperature in a suitable ether, e.g. THF, in the presence of an excess of acetic anhydride.

In step 3 of the second process according to the invention, the anhydride 7 is opened regioselectively with the amine $R^1R^2NH$ to form the unsaturated monoamide 8. $R^1$ and $R^2$ are as defined above. In principle, the reaction can be carried out in any inert solvent and over a wide temperature range (e.g. approx. −40° C. to +100° C.). For given reactants, solvent and reaction temperature, the regioselectivity can be significantly increased by adding the amine in portions to the suspension of the anhydride 7 over a prolonged period. The reaction of 7 with the preferred amines $R^1R^2NH$ can be carried out in polar and apolar solvents, preferably in the solvent ethyl acetate at 0°–30° C. The reaction gives a high yield after 4 hours to 2 days. The regioisomeric unsaturated monoamides of the crude product can be separated by HPLC. Direct hydrogenation of the crude product in methanolic solution over palladium-on-charcoal gives the racemic saturated monoamide of formula 1 and its regioisomers, which can easily be separated by HPLC. The ratio of the regioisomers in the crude unsaturated monoamide can be determined in this way. The ratio of the regioisomers can be improved by crystallization, e.g. from MTB ether.

In step 4 of the second process according to the invention, the unsaturated monoamide 8 is subjected to asymmetric hydrogenation, in the presence of a chiral transition metal diphosphine catalyst, to give 1 ($R^5=H$). The remarks made under step 2 of the first process according to the invention apply by analogy.

As already presented in concrete terms in German patent documents A-39 30 397 and A-39 33 096, the saturated monoamide 1 ($R^5=H$) can be reacted with primary or secondary amines to give the corresponding diamides, e.g. renin inhibitors, without racemization.

The following Examples further illustrate the two processes according to the invention and describe concrete procedural variants. For reasons relating to apparatus, the Examples on asymmetric hydrogenations were carried out in the present invention predominantly at room temperature under 1 atm of hydrogen, but the hydrogenation according to the invention can equally well be carried out at higher pressure values and other temperatures.

GENERAL WORKING TECHNIQUE AND ANALYTICAL CHEMISTRY

The optical purities of batches of 2-benzylsuccinic acid 5 from asymmetric hydrogenations were confirmed by HPLC separation of both enantiomeric dimethyl esters (prepared by reacting 5 with an excess of diazomethane) on the chiral phase ®CHIRALCEL OC with n-hexane/isopropanol (75:25), 0.5 ml/min, room temperature, 220 nm detector. The (R) isomer ($R^3=R^4=H$, dimethyl ester) is eluted after 14.30 minutes and the corresponding (S) isomer after 16.46 min.

The optical purities of the monoamides ($R^5=H$) from asymmetric hydrogenations of 8 were determined by two independent analytical methods. In the first analytical method, monoamides 1 ($R^5=H$) were reacted with excess diazomethane to give the monomethyl ester monoamide and its two enantiomers were separated (on ®CHIRALCEL OC with n-hexane/isopropanol (70:30 to 50:50), 1.0 ml/min, 35° C., 220 nm detector). In the second analytical method, monoamides 1 ($R^5=H$) were reacted with optically pure (S)(−)-1-phenylethylamine under catalysis to give the corresponding diamides 34.

If the compound 1 ($R^5=H$) is not optically pure, this reaction yields a mixture of two diastereoisomeric compounds 34, namely the products of RS and SS configurations.

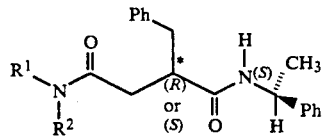

EXAMPLES

Example 1

Step 1: (E)-Phenylitaconic acid (formula 4, $R^3=R^4=H$)

4.0 kg (35.7 mol, 1.21 equivalents based on benzaldehyde) of potassium tert-butylate are added to 21.0 l of tert-butanol at room temperature under $N_2$, with stirring. The mixture is heated to 55° C. and stirred until a clear solution is formed (approx. 30–60 min). At a jacket temperature of 0° C., the solution is cooled to an internal temperature of 20° C., the potassium tert-butylate separating out as a very finely divided precipitate. 6.0 l (36.1 mol, 1.22 equivalents based on benzaldehyde) of diethyl succinate, cooled to 0° C. beforehand, are poured in over 5 min. The mixture is stirred for 5 min and 3.0 l (3.13 kg, 29.5 mol, 1.0 equivalent) of benzaldehyde are then poured in over 5–10 min (again at a jacket temperature of 0° C.). The exothermic reaction causes the internal temperature to rise to 32°–36° C. The mixture is stirred for 20 min, the internal temperature dropping to 10°–15° C. 18.0 l of 10% aqueous sodium hydroxide solution are run in and the mixture is then stirred for 30 min at an internal temperature of 75° C. It is cooled to 40° C. and the water phase is separated off. The butanol phase is extracted once with 10 l of 2 molar sodium hydroxide solution and twice with 5 l of 2 molar sodium hydroxide solution each time. The combined aqueous phases (approx. 40 l) are washed once with 10 l and once with 5 l of methyl tert-butyl ether and then adjusted to pH 7.5 with approx. 5–10 l of 37% hydrochloric acid at 15°–20° C. 20 l of ethyl acetate are run into this aqueous phase and the pH is then adjusted to 3.0 with approximately a further 5 l of 37% hydrochloric acid. The water phase is separated off and extracted once with 10 l and then twice with 5 l of ethyl acetate. The combined ethyl acetate extracts are concentrated to 10 l under vacuum. 12 l of butyl acetate are added and the residual ethyl acetate is removed under vacuum. The suspension formed is stirred for one hour at 10° C. and the solid is separated off by centrifugation. It is washed with twice 2 l of butyl acetate, cooled to 0°–10° C. beforehand, and then with twice 2 l of diisopropyl ether and dried by centrifugation. The product is suspended in 15 l of water, stirred for 12 hours, separated off by centrifugation, washed with water, dried by centrifugation and then dried to constant weight at 40° C. under vacuum.

This gives 3.1 kg (15.0 mol, yield 51% of theory based on benzaldehyde) of a colorless solid, m.p. 185°–188° C.

$^1H$ NMR (DMSO-$d_6$):δ = 12.5 (s, 2H, $CO_2H$), 7.74 (s, 1H, =CH), 7.20–7.55 (m, 5H, arom. H), 13.38 (s, 2H, $CH_2$) ppm.

Step 2: Optically active benzylsuccinic acid (formula 5, $R^3=R^4=H$) by the asymmetric hydrogenation of (E)-phenylitaconic acid Table 1 gives an overview of the asymmetric hydrogenations of (E)-phenylitaconic acid carried out, the optical inductions thereby achieved and the corresponding reaction parameters. The preparation of the novel chiral diphosphines 23, 30, 31 and 32 and of the isolated cationic rhodium(I) complexes of 31 and 32 is described after the Examples of the two processes according to the invention (vide infra). Five of these hydrogenations are described in detail in order to illustrate the experimental procedure further:

a) Hydrogenation using the neutral rhodium(I) complex of (2R,4R)(+)-BPPM (formula 21) in the presence of (R)(+)-1-phenylethylamine A suspension of 22.7 mg (0.092 mmol of Rh) of bis(1,5-cyclooctadiene)dirhodium(I) dichloride (Fluka) in 5 ml of analytical-grade methanol is degassed in a shaking duck by having a stream of argon bubbled through it. 55.4 mg (0.10 mmol) of (+)-BPPM are added and the solution formed is degassed for a further 15 min. In a second vessel, 1.03 g (5.0 mmol) of (E)-phenylitaconic acid are dissolved in 5 ml of analytical-grade methanol, 606 mg (5.0 mmol) of (+)-phenylethylamine (Aldrich) are added and this solution is also flushed with argon. It is then poured into the solution in the shaking duck. The shaking duck is connected to a hydrogen supply vessel and the argon atmosphere is displaced several times with hydrogen. The solution is then shaken at room temperature (25° C.) under a constant 1 atm of $H_2$ for 16 hours. Approx. 120 ml of $H_2$ gas are taken up (100% of theory). HPLC (eluent:water-/acetonitrile 3:1 containing 1.5 g of $NH_4H_2PO_4$ per liter of eluent and adjusted to pH 3.5 with concentrated phosphoric acid) indicates quantitative conversion of the phenylitaconic acid ($t_{ret}$ 7.74 min) to benzylsuccinic acid ($t_{ret}$ 6.74 min). The hydrogen in the shaking duck is displaced with nitrogen and 15 ml of 2N hydrochloric acid are then added dropwise, with cooling. The solid is filtered off with suction and the filtrate is extracted with three times 30 ml of MTB ether. The combined extracts are washed with three times 40 ml of 2N hydrochloric acid and then dried and concentrated under vacuum and the residue is dried under high vacuum to give 900 mg (yield 87% of theory) of a colorless solid. This crude product has 95.5% ee of the (R) configuration according to ®CHIRALCEL OC analysis. The solid is boiled in 15 ml of water, 50 mg of activated charcoal are added and the mixture is boiled for 10 min. It is filtered hot and the material on the filter is rewashed with 10 ml of hot water. The filtrate is cooled at 0° C. for 12 hours and the solid which has crystallized out is filtered off with suction, washed with 5 ml of ice-water and dried under high vacuum.

630 mg (yield 61%) of a colorless solid, $[\alpha]_D^{25} = +26.3°$ (c=1.5, EtOAc). This recrystallized product has 99.2% ee according to ®CHIRALCEL OC analysis.

TABLE 1a

Asymmetric hydrogenations of phenylitaconic acid (formula 4) to optically active 2-benzylsuccinic acid (formula 5)

| No | Ex. | t (°C.)/ reaction time | Diphosphine | Formula | Complex formula | Substrate/ catalyst ratio | Additive (eq. based on substrate) | |
|---|---|---|---|---|---|---|---|---|
| 1 | — | 45° C./40 h | (−)-BPPM | 20 | a) | 66 | (−)- $PhCH(CH_3)NH_2$ | (2.0) |
|   |   |   |   |   |   |   | $HCO_2H$ | (10.0) |
| 2 | — | 55° C./25 h | (−)-BPPM | 20 | a) | 80 | (−)- $PhCH(CH_3)NH_2$ | (2.0) |
|   |   |   |   |   |   |   | $HCO_2H$ | (15.0) |
| 3 | — | 30° C./40 h | (−)-BPPM | 20 | a) | 16 | (−)- $PhCH(CH_3)NH_2$ | (2.0) |
|   |   |   |   |   |   |   | $HCO_2H$ | (15.0) |
| 4 | — | 25° C./16 h | (−)-BPPM | 20 | 11 | 50 | $NEt_3$ | (1.0) |
| 5 | — | 25° C./16 h | (−)-BPPM | 20 | 11 | 50 | (−)- $PhCH(CH_3)NH_2$ | (1.0) |
| 6 | — | 25° C./16 h | (−)-BPPM | 20 | 11 | 50 | (+)- $PhCH(CH_3)NH_2$ | (1.0) |
| 7 | 1a) | 25° C./16 h | (+)-BPPM | 21 | 11 | 50 | (+)- $PhCH(CH_3)NH_2$ | (1.0) |
| 8 | 1b) | 25° C./5 h | (+)-BPPM | 21 | 11 | 200 | $NEt_3$ | (1.0) |
| 9 | — | 25° C./16 h | (+)-BPPM | 21 | 11 | 1000 | $NEt_3$ | (1.0) |
| 10 | — | 25° C./16 h | (+)-BPPM | 21 | 11 | 200 | $(C_6H_{11})_2NEt$ | (1.0) |
| 11 | 1c) | 25° C./4 h | (+)- phenyl-CAPP | 23 | 11 | 100 | — | |
| 12 | — | 25° C./5 h | (+) | 24 | 11 | 200 | $NEt_3$ | (1.0) |
| 13 | — | 25° C./48 h | (−)- Norphos | 25 | 11 | 200 | $NEt_3$ | (1.0) |
| 14 | — | 25° C./24 h | (+)- DIOP | 26 | 13 | 1000 | $NEt_3$ | (1.0) |
| 15 | — | 25° C./4 h | (−)- phenyl-β-glup | 27 | 11 | 200 | $NEt_3$ | (1.0) |
| 16 | 1d) | 25° C./48 h | (−)- phenyl-β-glup | 27 | 13 | 200 | $NEt_3$ | (1.0) |

TABLE 1b

Asymmetric hydrogenations of phenylitaconic acid (formula 4) to optically active 2-benzylsuccinic acid (formula 5)

| No. | Solvent | $H_2$ pressure (bar) | Crude yield % after working-up | Crude ee % after working-up | Pure yield % | Pure ee % | Absolute configuration |
|---|---|---|---|---|---|---|---|
| 1 | DMSO | 1 | 100 | — | 77 | 31 | (R) |
| 2 | DMSO | 1 | 100 | 28 | 52 | 24 | (R) |
| 3 | DMSO | 1 | 75 | — | 40 | 15 | (S) |
| 4 | $CH_3OH$ | 1 | 90 | 94 | 60 | 98.4 | (S) |
| 5 | $CH_3OH$ | 1 | 80 | 95 | 60 | 98.5 | (S) |
| 6 | $CH_3OH$ | 1 | 80 | 96 | 55 | 99.5 | (S) |
| 7 | $CH_3OH$ | 1 | 87 | 95.5 | 61 | 99.2 | (R) |
| 8 | $CH_3OH$ | 1 | 92 | — | 75 | 97.0 | (R) |
| 9 | $CH_3OH$ | 1 | 70[b] | — | 50 | 86.3 | (R) |
| 10 | $CH_3OH$ | 1 | 86 | — | 60 | 95.0 | (R) |
| 11 | $CH_3OH/C_6H_6$ 3:1 | 1 | 96 | 96 | 63 | 98.5 | (R) |

TABLE 1b-continued

Asymmetric hydrogenations of phenylitaconic acid (formula 4) to optically active 2-benzylsuccinic acid (formula 5)

| No. | Solvent | $H_2$ pressure (bar) | Crude yield % after working-up | Crude ee % after working-up | Pure yield % | Pure ee % | Absolute configuration |
|---|---|---|---|---|---|---|---|
| 12 | $CH_3OH$ | 1 | 96 | — | 70 | 3 | (R) |
| 13 | $CH_3OH$ | 1 | 50[c] | 57 | — | — | (R) |
| 14 | $CH_3OH$ | 1 | 90 | 62 | — | — | (R) |
| 15 | $CH_3OH$ | 1 | 95 | — | 75 | 4 | (R) |
| 16 | $CH_3OH$ | 1 | 75[b] | 65 | 60 | 59 | (R) |
| 17 | $CH_3OH$ | 1 | 96 | 3 | — | — | (R) |
| 18 | $CH_3OH$ | 1 | 35[d] | 22 | — | — | (R) |
| 19 | $CH_3OH$ | 1 | 95 | 10 | 65 | 7 | (S) |
| 20 | $CH_3OH$ | 50 | 92 | 60 | 75 | 64 | (R) |
| 21 | iPrOH/$C_6H_6$ 1:1 | 50 | 75[e] | 73 | 60 | 71 | (R) |
| 22 | $CH_3OH$ | 30 | 50[c] | 32 | — | — | (R) |

[a]asymmetric catalytic transfer hydrogenation; use of rhodium(II) acetate hydrate; procedure analogous to H. Brunner et al. (Synthesis, 743 (1989));
[b]approx. 25% of starting material unconverted;
[c]approx. 50% of starting material unconverted;
[d]approx. 65% of starting material unconverted;
[e]by-products are formed b) Hydrogenation using the neutral rhodium(I) complex of (2S,4S)(+)-BPPM (formula 21) in the presence of triethylamine A degassed solution of 100 g (0.48 mol) of (E)-phenylitaconic acid in 1.0 l of methanol and 67 ml (0.48 mol) of triethylamine is added to a solution of 0.54 g (1.1 mmol) of bis(1,5-cyclooctadiene)dirhodium(I) dichloride and 1.33 g (2.4 mmol) of (+)-BPPM in 460 ml of methanol, which is contained in a shaking duck and has been flushed with argon. The solution formed is shaken at room temperature under 1 atm of hydrogen gas. 10 l of $H_2$ are taken up over 5 hours and HPLC (see above) indicates quantitative hydrogenation. 1.5 l of 2N hydrochloric acid are added dropwise, with ice cooling (IT<30° C.). The precipitate is filtered off with suction and the filtrate is concentrated to approx. 1.5 l under vacuum. The concentrate is extracted once with 2 l and twice with 1 l of MTB ether and the combined extracts are washed with four times 1 l of 2N hydrochloric acid. The ether phase is dried, concentrated to dryness under vacuum (93 g of solid), taken up in 1.5 l of water and heated to the boil, 3 g of activated charcoal are added and the mixture is boiled for 10 min. It is filtered hot and the material on the filter is rewashed with twice 100 ml of boiling water. The filtrate is kept for 3 days at 0° C. and the solid which has crystallized out is filtered off with suction, washed with 500 ml of ice-water and dried over $P_2O_5$ under high vacuum.

This gives 74.6 g (0.36 mol, yield 75% of theory) of a colorless solid, $[\alpha]_D^{25}=+25.7°$ (c=1.5, EtOAc), 97% ee of the (R) configuration according to ®CHIRALCEL OC analysis.

c) Hydrogenation using the neutral rhodium(I) complex of (2R,4R)(+)-phenyl-CAPP (formula 23) without the addition of a base A degassed solution of 5.12 g (25.0 mmol) of (E)-phenylitaconic phenylitaconic acid in 22 ml of absolute methanol and 8 ml of benzene is added to a solution of 62 mg (0.125 mmol) of bis(1,5-cyclooctadiene)dirhodium(I) dichloride and 155 mg (0.27 mmol) of (+)-phenyl-CAPP in 15 ml of absolute methanol and 5 ml of benzene, which has been flushed with argon. The solution is shaken at room temperature under 1 atm of $H_2$. The uptake of $H_2$ starts after a few minutes. 550 ml of $H_2$ gas (100% of theory) are taken up over 4 hours and HPLC (see above) indicates quantitative hydrogenation. The solution is flushed with nitrogen and 40 g of ice and 40 ml of 2N hydrochloric acid are then added. A comparatively large amount of a yellowish solid precipitates. 100 ml of MTB ether are added and the mixture is stirred thoroughly. The small amount of solid remaining is filtered off with suction and washed with MTB ether. The organic phase of the filtrate is separated off and the aqueous phase is extracted again with three times 100 ml of MTB ether. The combined ether phases are washed with twice 100 ml of 1N hydrochloric acid and then dried and the solvent is removed under vacuum. The residue is dried under high vacuum to give 5.0 g (24.0 mmol, yield 96% of theory) of an off-white solid. This crude product has 96% ee of the (R) configuration according to ®CHIRALCEL OC analysis.

The crude product is taken up in 75 ml of water and 300 mg of activated charcoal are added at the boil. The mixture is boiled for 10 min and filtered hot with suction and the material on the filter is rewashed with 10 ml of hot water. The filtrate is kept for 2 days at 0° C. The crystals are filtered off with suction, washed with 25 ml of ice-water and dried over $P_2O_5$ under high vacuum to give 3.26 g (15.7 mmol, 63% of theory) of a colorless solid, m.p. 164°-165° C., $[\alpha]_D^{25}=+26.9°$ (c=1.45, EtOAc). This solid has 98.5% ee of the (R) configuration according to ®CHIRALCEL OC analysis.

d) Hydrogenation using the cationic rhodium(I) complex of phenyl-$\beta$-glup (formula 27) without the addition of a base A solution of 39 mg (0.055 mmol) of phenyl-$\beta$-glup (ISIS-Chemie) in 50 ml of analytical-grade methanol, which had been flushed with argon, was placed in a shaking duck containing 20 mg (0.05 mmol) of bis(1,5-cyclooctadiene)rhodium(I) tetrafluoroborate (Aldrich) under an argon atmosphere. A solution of 2.06 g (10.0 mmol) of (E)-phenylitaconic acid in 100 ml of methanol, which had been flushed with argon, was added and the resulting solution was shaken under 1 atm of hydrogen. A slow uptake of $H_2$ ceased completely after 48 hours, at which point 215 ml had been taken up. HPLC indicated 75% of product and 25% of starting material. The solution was flushed with $N_2$, 60 ml of MTB ether and 32 ml of 1N hydrochloric acid were added and the mixture was stirred for 15 min. The solid was filtered off with suction. The organic phase of the filtrate was separated off and the aqueous phase was extracted with 40 ml of MTB ether. The combined organic phases were washed with twice 30 ml of 0.5N hydrochloric acid and then dried, the solvent was removed under vacuum and the residue was dried under high vacuum to give 2.1 g (100% of theory) of a mixture of oil and solid, $[\alpha]_D^{22} = +10.2°$ (c=1.44, EtOAc). Allowing for the (E)-phenylitaconic acid content of approx. 25%, the ee of the (R)-benzylsuccinic acid is calculated to be approx. 55%. ®CHIRALCEL OC analysis, in which both enantiomers of the product are separated well from the starting material, gave 65% ee. After recrystallization from hot water/activated charcoal (as in c)), the ee had dropped to 58.6%.

e) Hydrogenation using the cationic ruthenium(II) complex (formula 16) of (S)(−)-BINAP (formula 33)

The ruthenium(II) complex was prepared in accordance with the communication by K. Mashima et al., J. Chem. Soc., Chem. Commun., 1208 (1989), and is described in detail in the present patent application (vide infra).

5.15 g (25 mmol) of (E)-phenylitaconic acid and 28 mg (0.025 mmol) of the complex RuI[((S)-BINAP)-(p—CH₃—C₆H₄—CH(CH₃)₂)]+I− were added to 50 ml of methanol through which argon had been bubbled. The mixture was then shaken in an autoclave for 1 day at 20° C. under 30 bar of H₂. HPLC indicated 52% of starting material and 48% of product. The solvent was removed under vacuum, the residue was taken up in 150 ml of MTB ether, and 5 ml of 1N hydrochloric acid were added. The precipitate was filtered off with suction. The MTB ether phase of the filtrate was separated off, washed with 10 ml of water and then dried and the solvent was removed under vacuum. Yield:5.2 g (100% of theory). The hydrogenated product component has 32% ee of the (R) configuration according to °CHIRALCEL OC analysis.

$[\alpha]_D^{20} = +3.9°$ (c=1.45, EtOAc). Because of the unhydrogenated phenylitaconic acid content of 52%, the calculated optical purity of 14.3% ee also leads to approx. 30% ee of the hydrogenated product component.

Step 3: Optically active bis(p-nitrophenyl) (R)-benzylsuccinate, formula 6 ($R^3=R^4=H$, $R^5=p$-nitrophenyl)

158 g (0.757 mol, 2.0 equivalents) of phosphorus pentachloride are added all at once to a suspension of 78.9 g (0.378 mol) of (R)-benzylsuccinic acid (97% ee) in 800 ml of toluene and the mixture is heated gently to 40° C. under N₂. A vigorous evolution of HCl gas occurs in an initially slightly exothermic reaction. The mixture is stirred for one hour at 40° to max. 45° C. The toluene is substantially stripped off under vacuum at a bath temperature of 35° C. The residual yellow oil (110 g, theory 92 g, i.e. 18 g of residual toluene) is dissolved in 400 ml of methylene chloride in the absence of moisture and 111 g (0.794 mol, 2.09 equivalents) of p-nitrophenol are added. The greenish suspension is cooled to 15° C. and 97 g (0.95 mol, 2.5 equivalents) of triethylamine are added dropwise over 40 min. A clear solution is formed after ⅛ to ½ of the amine has been added, and returns to a suspension as the dropwise addition is continued. The internal temperature is kept at 15°-20° C. throughout the whole of the dropwise addition. The mixture is then stirred for 20 hours at room temperature. It is diluted with 500 ml of methylene chloride and then stirred with four times 500 ml of semiconcentrated sodium carbonate solution for 5 min each time. The aqueous phases are each separated off. The combined aqueous phases are filtered and extracted again with 500 ml of methylene chloride. The combined methylene chloride phases are washed with 500 ml of water and then dried and the solvent is removed under vacuum to give 156 g (0.346 mol, 92% of theory) of a greenish brown solid as the crude product. This is dissolved in 500 ml of methylene chloride to give a clear solution, this solution is cooled to 0° C. and 3.5 l of diisopropyl ether are added dropwise over 30 min, with stirring. After approx. 600 ml, a thick pulp is formed which is difficult to stir; this becomes a readily stirrable suspension as the addition is continued. The solid is filtered off cold with suction, washed with 500 ml of cold diisopropyl ether, dried with suction and dried under high vacuum to give 137 g (0.304 mol, 80% of theory) of a light gray solid, m.p. 114°-118° C. (decomposition).

¹H NMR (CDCl₃):δ=8.2-8.3 (m, 4H, arom. H), 7.2-7.45 (m, 7H, arom. H), 7.10 (m, 2H, arom. H), 3.50 (m, 1H, CHCH₂Ph), 3.25 (dd, 1H), 3.0-3.2 (m, 2H), 2.88 (dd, 1H) ppm.

MS (DCI, isobutane): m/e=451 (M+H+), 312 (M+-nitrophenol), 173 (M+-2×nitrophenol-H).

A dinitrophenyl ester of lower melting point (104°-106° C.) was obtained starting from racemic benzylsuccinic acid.

Step 4: Optically active 2(R)-benzylsuccinic acid 1-(p-nitrophenyl) ester 4-(4-Boc-amino-1-piperidide) (formula 1, $R^1R^2N$=4-Boc-aminopiperidyl, $R^3=R^4=H$, $R^5=p$-nitrophenyl)

60 g (0.30 mol) of 4-Boc-aminopiperidine are added over 10 min at −10° C. under N₂ to a solution of 135 g (0.30 mol) of the (R)-diester (step 3) in 1.0 l of N,N-dimethylformamide. The mixture is stirred for 45 min at 0° C. TLC (silica gel, CH₂Cl₂/EtOAc 5:1) indicates complete conversion of the diester ($R_f$=0.87) to the product ($R_f$=0.35) and p-nitrophenol ($R_f$=0.59).

6.5 l of water and 1.2 l of methylene chloride are added, the mixture is stirred thoroughly and the organic phase is separated off. The aqueous phase is extracted again with twice 1.0 l of methylene chloride. The combined organic phases are washed with four times 250 ml of 0.5N sodium hydroxide solution in order to remove the nitrophenol. This is followed by washing with 250 ml of water. The methylene chloride phase is dried and the solvent is removed under vacuum to give 144.3 g (0.282 mol, 94% of theory) of a light brown foam as the crude product. Crystallization is effected from acetonitrile to give 94.2 g (0.184 mol, 62% of theory) of a colorless solid, m.p. 103°-105° C., $[\alpha]_D^{25} = +23.9°$ (c=1.54, EtOAc).

¹H NMR (CDCl₃):δ=8.20 (dd, 2H, arom. H), 7.2-7.4 (m, 5H, arom. H), 7.08 (m, 2H, arom. H), 4.4-4.5 (m, 2H, CO—N—CH₂), 3.6-3.8 (m, 2H, CO—N—CH₂), 3.40 (m, 1H, NHCH), 3.10 (m, 2H, N—CO—CH₂), 2.68-3.00 (m, 3H, NH and PhCH₂), 2.58 (dt, 1H, PhCH₂CH), 1.9-2.1 (broad t, 2H, NH—CH—CH₂), 1.44 (s, 9H, tert-Bu), 1.20-1.47 (m, 2H, NH—CH—CH₂). MS (DCI, isobutane): m/e=512 (M+H+), 456, 373.

EXAMPLE 2

Reaction of the Active Ester of Formula 1 (Process 1, Step 4) With Aliphatic Amines, Without Racemization 2.56 g (5.0 mmol) of the active ester (process 1, step 4) are dissolved in 25 ml of DMF to give a clear solution. 770 mg (6.35 mmol) of (S)(−)-1-phenylethylamine are added and the mixture is then heated at 40°-45° C. for 3 hours. TLC (CH$_2$Cl$_2$/EtOAc 5:1) indicates complete conversion of the active ester (R$_f$=0.26) to the product (R$_f$=0.1) and p-nitrophenol (R$_f$=0.64), and only small residues of the amine (R$_f$=0.04). The mixture is cooled to 0° C., 150 ml of water are added and extraction is carried out with 2×50 ml of methylene chloride. The extracts are dried and the solvent is removed under high vacuum to give 2.3 g (4.66 mmol, 93% of theory) of a crude product (oil/solid mixture). HPLC of the crude product on MOS Hypersil under the conditions given in the section "General working technique and analytical chemistry" indicates only the (RS) diastereoisomer of formula 34 (t$_{ret}$ 8.05 min) and not the (SS) diastereoisomer of 34 (t$_{ret}$ 7.58 min). If the racemic active ester of formula 1 is used as the starting material, the two diastereoisomers of 34 are obtained in a ratio of 1:1.

To remove the p-nitrophenol from the crude product, the latter is dissolved in 100 ml of acetonitrile with gentle heating, the solution is cooled to approx. 10° C., 200 ml of water are added and the mixture is stirred for 20 min in an ice bath. The solid is filtered off with suction and dried under vacuum to give 1.5 g of white crystals of the pure (RS) diastereoisomer of formula 34. Under corresponding reaction conditions, the active ester also gives amide formation, without racemization, with amines which are C-terminal parts of renin inhibitors (e.g. those in German patent document A-39 30 397).

EXAMPLE 3

Saponification of the Active Ester of Formula 1

50 ml of 0.1N sodium hydroxide solution (5.0 mmol) are added under N$_2$ to a solution of 2.56 g (5.0 mmol) of the active ester (Example 1, step 4) in 150 ml of acetonitrile and the mixture is heated at 40°-45° C. for 3 hours. As the reaction is still incomplete according to TLC, 80 mg (2.0 mmol) of sodium hydroxide are added and the mixture is stirred for a further 15 min at 40°-45° C. TLC now indicates only nitrophenol and the carboxylic acid of formula 1. The organic solvent is removed at 30° C. under vacuum. The aqueous residue is adjusted to pH 1 with 2N hydrochloric acid. The solid which precipitates is extracted with 2×50 ml of methylene chloride. The extracts are dried and the solvent is removed under vacuum. The crude product exhibits no optical rotation, [α]$_D^{20}$=0° (c=1.0, methanol) and is racemic according to ®CHIRALCEL OC analysis.

EXAMPLE 4

Examples of the Second Process According to the Invention

Step 1: Identical to Example 1, step 1
Step 2: Phenylitaconic anhydride (formula 7, R$^3$=R$^4$=H)

2.3 l (approx. 2.49 kg, approx. 24.4 mol) of acetic anhydride are added at 20° C. to a solution of 2.28 kg (11.1 mol) of (E)-phenylitaconic acid in 5.7 l of THF. The mixture is stirred for 5 hours at room temperature. After 1 hour there is a clear light yellow solution; after 3 hours the product begins to crystallize out. The THF is removed under vacuum, 5.0 l of methyl tert-butyl ether are added to the residue in order to complete the crystallization, and the product is filtered off with suction. It is washed with MTB ether, dried with suction and dried under vacuum at 40° C. Yield: 1.68 kg (8.94 mol, 81% of theory), m.p. 167°-170° C.

$^1$H NMR (DMSO-d$_6$):δ=7.63–7.73 (m, 3H, =CH+2 arom. H), 7.47-7.56 (m, 3H, 3 arom. H), 3.99 (d, 2H, CH$_2$) ppm.

Step 3: 2(E)-Benzylidenesuccinic acid 4-[4-(Boc-amino)-1-piperidide] (formula 8, R$^1$R$^2$N=4-Boc-aminopiperidyl, R$^3$=R$^4$=H)

2.81 kg (14.05 mol, 1.15 equivalents) of 4-(Boc-amino)piperidine are added in equal portions over 90 min at 24° C. to a suspension of 2.29 kg (12.2 mol) of phenylitaconic anhydride in 20 l of ethyl acetate. The mixture is stirred for a further 4 hours at 25° C. to give a thick white precipitate. 20 l of MTB ether are run in over 30 min and the suspension is stirred for 2 hours at 10° C. The solid is filtered off with suction and washed with twice 2 l of MTB ether. It is dried with suction and then dried at 40° C. under vacuum. Yield:3.76 kg (9.7 mol, 80% of theory) of a colorless solid, m.p. 157°-160° C.

$^1$H NMR (DMSO-d$_6$):δ=12.47 (s, 1H, CO$_2$H), 7.72 (s, 1H, =CHPh), 7.30-7.50 (m, 5H, arom. H), 6.92 (d, 1H, NHBoc), 4.23 (d, 1H, CO—NCH$_2$), 3.88 (d, 1H, CO—$\overline{\text{N}}$CH$_2$), 3.50 (broad m, 1H, N$\overline{\text{H}}$—CH), 3.45 (s, 2H, N—$\overline{\text{CO}}$—CH$_2$—C=), 3.10 (t, 1H, C$\overline{\text{O}}$—NCH$_2$), 2.74 (t, 1H, $\overline{\text{CO}}$—NCH$_2$), 1.76 (m, 2H, NH—CH—CH$_2$), 1.39 [s, 9H, $\overline{\text{C}}$(CH$_3$)$_3$], 1.14–1.38 (m, 2H, NH—C$\overline{\text{H}}$—CH$_2$) ppm.

Determination of the ratio of the regioisomers by symmetric hydrogenation/HPLC analysis gave >90% of the 4-amide.

Step 4: Optically active 2(R)-benzylsuccinic acid 4-[4-(Boc-amino)-1-piperidide] (formula 1, R$^1$R$^2$N=4-Boc-amino-piperidyl, R$^3$=R$^4$=H, R$^5$=H)

Table 2 gives an overview of the asymmetric hydrogenations of step 3 carried out, the optical inductions thereby achieved and the corresponding reaction parameters. The preparation of the novel chiral diphosphines 23, 30, 31 and 32 and of the isolated cationic rhodium(I) complexes of 31 and 32 is described after the Examples of the two process according to the invention (vide infra). Three of these hydrogenations are described in detail in order to illustrate the experimental procedure further:

a) Hydrogenation using the cationic rhodium(I) complex of (3R,4R)(+)-1-phenylaminocarbonyl-3,4-bis(diphenylphosphino)pyrrolidine (formula 1) under an H$_2$ pressure of 50 bar 18.5 g (21.6 mmol, substrate/catalyst ratio 100:1) of [(3R,4R)-1-phenylaminocarbonyl-3,4-bis(diphenylphosphino)pyrrolidine-P,P'](1,5-cyclooctadiene)rhodium tetrafluoroborate are added to a solution of 840 g (2.16 mol) of step 3 in 11 l of analytical-grade methanol, through which argon has been bubbled. The mixture is hydrogenated for 24 hours at 20° C. under an H$_2$ pressure of 50 bar. HPLC analysis indicates a quantitative reaction. The solvent is completely removed under vacuum at a bath temperature of 30° C. The residue is taken up in 20 l of MTB ether and extracted by stirring with 8 l of 0.5N hydrochloric acid. The water phase is extracted with twice 5 l of MTB ether. The combined ether phases are washed with twice 2 l of 0.5N hydrochloric acid and then dried. The solvent is removed under vacuum and the residue is dried to constant weight under high vacuum. The crude product (800 g) shows about 80% ee of the (R) configuration when analyzed on ®CHIRALCEL OC.

The crude product is suspended in 10 l of diethyl ether and crystallized from methanol/diisopropyl ether. Yield:687 g (1.76 mol, 81.3% of theory) of a colorless solid, m.p. 135°-136° C. ®CHIRALCEL OC analysis gives 93% ee of the (R) configuration.

$^1$H NMR (DMSO-d$_6$):δ=12.05 (s, 1H, CO$_2$H), 7.32–7.15 (m, 5H, arom. H), 6.75–6.90 (broad dd, 1H, NH), 4.15 (broad d, 1H, NCH), 3.71 (broad d, 1H, NCH), 3.43 (broad s, 1H, NCH), 2.53–3.05 (m, 6H, CO—CH$_2$, Ph—CH$_2$, NCH), 2.27 (dd, 1H, CHCO$_2$H), 1.68 (broad t, 2H, NCHCH$_2$), 1.36 (s, 9H, C(CH$_3$)$_3$), 1.05–1.25 (m, 2H, NCHCH$_2$) ppm.

material is filtered off with suction. The aqueous phase of the filtrate is extracted again with 50 ml of MTB ether. The combined ether phases are washed with twice 20 ml of 0.5N hydrochloric acid and then dried. The solvent is removed under vacuum and the residue is dried under high vacuum to give 4.5 g (11.5 mmol, 92% of theory) of a white foam as the crude product, which has 85% ee of the (R) configuration according to ®CHIRALCEL OC analysis.

TABLE 2a

Asymmetric hydrogenations of 2(E)-benzylidenesuccinic acid 4-[4-(Boc-amino)-1-piperidide] (formula 8) to optically active 2(R)-benzylsuccinic acid 4-[4-(Boc-amino)-1-piperidide] (formula 1)

| No | Ex. | t (°C.)/ reaction time | Diphosphine | Formula | Complex formula | Substrate/ catalyst ratio | Additive (eq. based on substrate) |
|----|-----|------------------------|-------------|---------|-----------------|---------------------------|-----------------------------------|
| 1  | 4a) | 20° C./24 h | (+) | 31 | 13 | 100 | — |
| 2  | 4a$_1$) | 25° C./24 h | (+) | 31 | 13 | 100 | — |
| 3  | 4a$_2$) | 25° C./24 h | (+) | 32 | 13 | 100 | — |
| 4  | 4b | 20° C./24 h | (+) | 31 | 13 | 300 | — |
| 5  | — | 25° C./24 h | (+) | 31 | 13 | 200 | — |
| 6  | — | 25° C./24 h | (+) | 30 | 13 | 100 | — |
| 7  | 4c) | 25° C./2 h | (+)-phenyl-CAPP | 23 | 11 | 100 | — |
| 8  | — | 25° C./16 h | (−)-BDPP | 29 | 13 | 200 | — |
| 9  | — | 25° C./18 h | (−)-phenyl-β-glup | 27 | 13 | 200 | — |
| 10 | — | 25° C./24 h | (−)-BPPM | 20 | 11 | 230 | NEt$_3$ (0.96) |

$^{a)}$Approx. 10% of by-products visible in HPLC are formed.

TABLE 2b

Asymmetric hydrogenations of 2(E)-benzylidenesuccinic acid 4-[4-(Boc-amino)-1-piperidide] (formula 8) to optically active 2(R)-benzylsuccinic acid 4-[4-(Boc-amino)-1-piperidide] (formula 1)

| No. | Solvent | H$_2$ pressure (bar) | Crude yield % after working-up | Crude ee % after working-up | Pure yield % | Pure ee % | Absolute configuration |
|-----|---------|----------------------|--------------------------------|------------------------------|--------------|-----------|------------------------|
| 1   | CH$_3$OH | 50  | 95  | 80.4 | 81 | 93.0 | (R) |
| 2   | CH$_3$OH | 50  | 95  | 72.4 | 71 | 95.4 | (R) |
| 3   | CH$_3$OH | 50  | 95  | 81   | —  | —    | (R) |
| 4   | CH$_3$OH | 100 | 96  | 77   | 64 | 94.6 | (R) |
| 5   | CH$_3$OH | 100 | 100 | —    | 70 | 98.1 | (R) |
| 6   | CH$_3$OH | 50  | 98  | 67   | 75 | 67   | (R) |
| 7   | CH$_3$OH/C$_6$H$_6$ 2.5:1 | 1 | 92 | 85 | 72 | 94.0 | (R) |
| 8   | CH$_3$OH | 1   | 87$^{a)}$ | 31 | 60 | 29 | (R) |
| 9   | CH$_3$OH | 1   | 95  | 0    | —  | —    | racemic |
| 10  | CH$_3$OH | 1   | 95  | 18   | —  | —    | (S) |

$^{a)}$Approx. 10% of by-products visible in HPLC are formed.

a$_1$) An analogous reaction mixture (50 bar of H$_2$, substrate/catalyst ratio 100:1) with 7.76 g (20 mmol) of substrate gave a crude product with 72.4% ee and a recrystallized product in 70.5% yield and with 72.4% ee of the (R) configuration.

a$_2$) An analogous reaction mixture (50 bar of H$_2$, substrate/catalyst ratio 100:1) with 3.88 g (10 mmol) of substrate, using the catalyst [(3R,4R)-1-phenyl-aminocarbonyl-3,4-bis(di-p-tolylphosphino)-pyrrolidine-P,P'](1,5-cyclooctadiene)rhodium tetrafluoroborate, gave a crude product with 81% ee of the (R) configuration.

b) Hydrogenation under an H$_2$ pressure of 100 bar with a higher substrate/catalyst ratio 58 mg (0.068 mmol, substrate/catalyst ratio 300:1) of the complex as in a) were added to a solution of 7.8 g (20.1 mmol) of step 3 in 100 ml of methanol, through which argon had been bubbled. The mixture was then hydrogenated in a shaking autoclave for 24 hours at 20° C. under 100 bar of H$_2$. Working-up analogously to a) gave 7.55 g (96% of theory) of a crude product with 77% ee of the (R) configuration. Redissolution analogously to a) gave 5.0 g (64% of theory) of colorless crystals with 94.6% ee.

c) Hydrogenation at 1 bar of H$_2$ using the neutral rhodium(I) complex of (2R,4R)(+)-phenyl-CAPP (formula 23) in methanol/benzene 77.5 mg (0.135 mmol) of (2R,4R)-phenyl-CAPP are added to a suspension of 31 mg (0.125 mmol of Rh) of bis (1,5-cyclooctadiene)dirhodium(I) dichloride in 25 ml of methanol and 10 ml of benzene, through which argon has been bubbled. The clear solution formed is stirred for 15 min under argon and 4.85 g (12.5 mmol, substrate/catalyst ratio 100) of step 3 are then added. The argon atmosphere is displaced with hydrogen and the solution is then shaken at 24° C. under 1 bar of H$_2$. The theoretical amount (280 ml) of H$_2$ gas is taken up over 2 hours and HPLC indicates a quantitative reaction. The solvents are removed under vacuum. The residue is taken up in 100 ml of MTB ether and shaken with 40 ml of 0.5N hydrochloric acid and undissolved The solid is dissolved in 50 ml of diethyl ether, immediately giving rise again to the formation of a white precipitate. 10 ml of diisopropyl ether are added, the mixture is kept for 1 hour at −15° C. and the solid is filtered off with suction and washed with twice 10 ml of cold ether. It is dried under high vacuum to give 3.50 g (9.0 mmol, 72% of theory) of a colorless powder, m.p. 134°-135° C., with 94% ee of the (R) configuration. On standing, a further 350 mg precipitate from the mother liquor. Total yield:3.85 g (9.9 mmol, 79% of theory).

EXAMPLE 5

Preparation of Novel Chiral Diphosphines and Novel Rhodium Catalysts a) (2R,4R)(+)-Phenyl-CAPP (formula 23)

$a_1$) (2R)-Diphenylphosphinomethyl-(4R)-diphenylphosphinopyrrolidine 4.04 g (7.3 mmol) of (2R,4R)(+)-BPPM (formula 21, G. L. Baker, J. K. Stille et al., J. Org. Chem., 46, 2954 (1981)) are added at 0° C. to 20 ml of freshly distilled trifluoroacetic acid which has been flushed with argon, and the mixture is then stirred for 1 hour at 0° C. The trifluoroacetic acid is removed at 20° C. under vacuum and the vacuum is then let down with argon. The oily residue is dissolved in 20 ml of degassed methylene chloride, and 16 ml of a 10% aqueous ammonia solution, which has been flushed with argon, are added. The two-phase mixture is shaken in a separating funnel under argon and the organic phase is separated off, flushed with argon and washed with twice 10 ml of degassed water. The organic phase is dried under argon over 1 g of magnesium sulfate, the solvent is removed under vacuum and the residue is dried under high vacuum to give 2.8 g (6.15 mmol, 84% of theory) of a resin, $[\alpha]_D^{20} = +13.2°$ (c=1.0, benzene), from which a colorless solid, m.p. 103°-104° C., $[\alpha]_D^{20} = +15.75°$ (c=1.0, benzene), is obtained with appreciable losses by recrystallization from n-hexane under argon.

$^1$H NMR (CDCl$_3$):δ=7.2-7.5 (m, 20H, arom. H), 2.9-3.2 (m, 3H, NHC$\underline{H}_2$ and NHC$\underline{H}$CH$_2$), 2.80 (m, 1H, Ph$_2$PC$\underline{H}$), 2.42 (dd, 1H, Ph$_2$PC$\underline{H}_2$), 2.05-2.35 (m, 3H, NH and Ph$_2$PC$\underline{H}_2$ and C$\underline{H}_2$CHPPh$_2$), 1.38 (m, 1H, C$\underline{H}_2$CHPPh$_2$) ppm.

$a_2$) 1-Phenylaminocarbonyl-(2R)-diphenylaminomethyl-(4R)-diphenylphosphinopyrrolidine [(2R,4R)(+)-phenyl-CAPP]

A solution of 2.6 g (5.7 mmol) of the crude product of $a_1$) in 30 ml of methylene chloride and a solution of 0.72 g (6.0 mmol) of phenyl isocyanate in 30 ml of methylene chloride, which have been degassed with argon and cooled to 0° C., are combined and stirred for 15 min in an ice bath under argon. The solvent is removed under vacuum and the residue is chromatographed on 30 g of silica gel (35–70μ) under N$_2$ pressure using methylene chloride/0.1% triethylamine as the eluent to give 2.18 g (3.8 mmol, 67% of theory) of colorless crystals, m.p. 180°-182° C., $[\alpha]_D^{25} = +21.9°$ (c=0.5, benzene).

$^1$H NMR (CDCl$_3$):δ=7.2-7.6 (m, 24H, arom. H), 6.98 (m, 1H, arom. H), 5.80 (s, 1H, NH), 4.08 (m, 1H, NCH), 3.86 (t, 1H, NCH$_2$), 3.30 (dd, 1H, NCH$_2$), [2.99 (dt, 1H), 2.80- 2.95 (m, 1H), 2.30-2.42 (m, 1H), 2.28 (dd, 1H), C$\underline{H}_2$PPh$_2$ and C$\underline{H}_2$CHPPh$_2$], 1.98 (m, approximate qui, 1$\underline{H}$, CHPPh$_2$) ppm.

b) (3R,4R)(+)-1-Acetyl-3,4-bis(di-p-tolylphosphino)-pyrrolidine (formula 30)

$b_1$) Di(p-tolyl)phosphane is prepared according to J. Am. Chem. Soc., 95, 210 (1973), by reduction of the corresponding chlorophosphane with lithium aluminum hydride in refluxing diethyl ether, and is distilled under high vacuum: b.p. 135°-137° C./1 Torr, yield 71% of theory.

$b_2$) (3S,4S)-3,4-Bis(methylsulfonyloxy)pyrrolidinium bromide is prepared from L(+)-tartaric acid according to German Offenlegungsschrift 3403194 (disclosure date 1.8.1985).

$b_3$) (3R,4R)-3,4-Bis(di-p-tolylphosphino)pyrrolidinium chloride 3.56 g (155 mmol) of sodium are added to a solution of 33.15 g (155 mmol) of di(p-tolyl)phosphane in 150 ml of absolute THF and the mixture is refluxed for 5 hours under N$_2$, the sodium going substantially into solution by reacting. The residual sodium (0.2 g) is withdrawn and the THF is removed under vacuum. The residue is dissolved in 160 ml of absolutely degassed DMF which has been cooled to 0° C. beforehand, the solution is cooled to −30° C. and 13.6 g (40 mmol) of the hydrobromide of $b_2$) are added all at once. The reaction mixture becomes viscous for approx. 30 min and then becomes more fluid again. It is stored overnight at 0° C. in a refrigerator, in the absence of moisture. The DMF is tripped off under an oil-pump vacuum at a bath temperature of 40° C. 140 ml of water and 140 ml of ether (both degassed) are added to the solid reddish viscous residue, the organic phase is separated off, the water phase is extracted once more with 70 ml of ether and the combined ether phases are stirred overnight with 160 ml of 1N hydrochloric acid under argon. The white solid is filtered off with suction, dried under high vacuum and then recrystallized from 170 ml of isopropanol (degassed). The crystals are filtered off with suction, rewashed with isopropanol and dried under high vacuum.

Yield:12.7 g (60% of theory). Crystals sealed in a tube at approx. 200 Torr have a melting point of 238°–243° C.; on heating in an open melting point tube, the melting point is found to be 224°-228° C.

$[\alpha]_D^{20} = +171.6°$ (c=2.67 in 99% ethanol).

$^1$H NMR (CDCl$_3$):δ=10.02 (broad s, 2H, NH$_2^+$), 7.30 (m, 4H, arom. H), 6.93-7.18 (m, 8H, arom. H), 3.58 (m, 2H, C$\underline{H}_2$NH), 3.12 (m, 2H, C$\underline{H}_2$NH), 2.88 (m, 2H, CHAr$_2$), 2.36 (s, 6H, CH$_3$), 2.31 (s, 6H, CH$_3$) ppm.

$b_4$) (3R,4R)(+)-1-Acetyl-3,4-bis(di-p-tolylphosphino)pyrrolidine 3.20 g (6.0 mmol) of the hydrochloride ($b_3$) and 8 ml (47.0 mmol) of triethylamine are dissolved in 40 ml of degassed methylene chloride. 0.57 ml (628 mg, 8.0 mmol) of acetyl chloride is added over 5 min, with ice cooling. The mixture is stirred for 2 hours at room temperature, 100 ml of 2N sodium hydroxide solution are added and the mixture is stirred for a further 15 min. The organic phase is washed with water, 2N hydrochloric acid and water and dried, the solvent is removed under vacuum to 10 ml and the product is precipitated by the dropwise addition of 40 ml of n-pentane. It is filtered off with suction and dried under high vacuum. Yield:2.94 g (5.47 mmol, 91% of theory), m.p. 164°-167° C., $[\alpha]_D^{20} = +118°$ (c=0.036 in toluene).

$b_5$) [(3R,4R)-1-Acetyl-3,4-bis(di-p-tolylphosphino)-pyrrolidine-P,P'](1,5-cyclooctadiene)rhodium tetrafluoroborate A solution of 460 mg (0.85 mmol) of the acetylpyrrolidine of $b_4$) in 9 ml of degassed methylene chloride is added at room temperature to a solution of 347 mg (0.85 mmol) of bis(1,5-cyclooctadiene)rhodium tetrafluoroborate (Aldrich) in 3 ml of degassed methylene chloride. The mixture is stirred for 2 hours under argon and concentrated under vacuum to half its volume and the product is precipitated by the addition of ether. It is filtered off with suction under argon, dissolved in the minimum amount of methanol and reprecipitated by the addition of the 50-fold amount of degassed ether. The precipitate is filtered off with suction and dried under high vacuum to give 620 mg (0.74 mmol, 86% of theory) of a yellow solid.

$^1$H NMR (CD$_2$Cl$_2$):δ=7.77 (approximate t, 4H, arom. H), 7.25-7.50 (m, 12H, arom. H), 5.65 (m, 2H, olef. H), 4.53 (m, 2H, olef. H), 3.75 (m, 1H, NCH$_2$), 3.75 (approximate t, 1H, NCH$_2$), 2.70-3.22 (m, 4H, 2 times CHPAr$_2$ and 2 times NCH$_2$), 2.52 (s, 3H, CH$_3$), 2.50 (s, 3H, CH$_3$), 2.47 (s, 3H, CH$_3$), 2.45 (s, 3H, CH$_3$), 2.35-2.55 (m, 4H, allyl H of COD), 2.10-2.22 (m, 4H, allyl H of COD), 1.78 (s, 3H, CO—CH$_3$) ppm.

c) (3R,4R)(+)-1-Phenylaminocarbonyl-3,4-bis(di-p-tolylphosphino)pyrrolidine (formula 32)

c$_1$) (3R,4R)(+)-3,4-Bis(di-p-tolylphosphino)pyrrolidine 2.02 g (3.80 mmol) of the hydrochloride of b$_3$) are added to a degassed 2-phase mixture of 110 ml of diethyl ether and 27 ml (5.4 mmol) of 0.2N potassium hydroxide solution and the mixture is stirred under argon until a complete solution is formed (approx. 10 min). The ether phase is separated off and the aqueous phase is extracted with 50 ml of degassed diethyl ether. The combined ether phases are dried, the solvent is removed under vacuum and the residue is dried under high vacuum to give 1.95 g (3.9 mmol, yield 100%) of a white foam, m.p. 63°-65° C.

$^1$H NMR (CD$_3$OD):δ=7.28 (t, 4H, arom. H), 7.14 (d, 4H, arom. H), 6.90-7.16 (m, 8H, arom. H), 4.83 (s, 1H, NH), 3.23-3.40 (m, 1H, Ar$_2$PCH), 2.70-2.88 (m, 4H, NCH$_2$), 2.28-2.42 (m, 1H, Ar$_2$PCH), 2.30 (s, 12H, CH$_3$) ppm. The compound was reacted without further purification.

c$_2$) (3R,4R)(+)-1-Phenylaminocarbonyl-3,4-bis(di-$p$-tolylphosphino)pyrrolidine 500 mg (4.2 mmol) of phenyl isocyanate are added dropwise, with ice cooling, to a solution of 1.87 g (4.0 mmol) of the product of c$_1$) in 30 ml of methylene chloride, through which argon has been bubbled, and the mixture is then stirred for 30 min at room temperature. 10 ml of water are added dropwise, the mixture is stirred for 15 min, the aqueous phase is separated off and the organic phase is diluted with 60 ml of degassed methylene chloride and then extracted with twice 20 ml of 2N hydrochloric acid followed by 20 ml of water. The organic phase is dried, the solvent is removed under vacuum and the residue is dried under high vacuum to give 2.08 g (3.55 mmol, 89% of theory) of a crude product. This is dissolved in 5 ml of methylene chloride, and 40 ml of degassed n-hexane are added dropwise, causing a permanent turbidity. The suspension is cooled at 0° C. for 12 hours and the solid is filtered off with suction, washed with n-hexane and dried under high vacuum to give 1.92 g (3.12 mmol, 83% of theory) of a colorless solid, $[\alpha]_D^{20}$=93.2° (c=2.04, benzene).

On heating, decomposition with the evolution of gas occurs at 110°-120° C. TLC:cyclohexane/ethyl acetate 3:1, R$_f$=0.40.

$^1$H NMR (DMSO-d$_6$):δ=8.14 (s, 1H, NH), 6.85-7.48 (m, 21H, arom. H), 3.84 (m, 2H, NCH$_2$), 3.38 (t, 2H, NCH$_2$), 2.85 (t, 2H, CHPAr$_2$), 2.30 (s, 6H, 2xCH$_3$), 2.28 (s, 6H, 2xCH$_3$) ppm.

c$_3$) [(3R,4R)(+)-1Phenylaminocarbonyl-3,4-bis(di-$p$-tolylphosphino)pyrrolidine-P,P'](1,5-cyclooctadiene)rhodium tetrafluoroborate A solution of 935 mg (1.52 mmol) of the product of c$_2$) in 23 ml of methylene chloride is added at room temperature under argon to a solution of 630 mg (1.55 mmol) of bis(1,5-cyclooctadiene)rhodium tetrafluoroborate in 6 ml of degassed methylene chloride. The mixture is stirred for 2 hours. TLC (CH$_2$Cl$_2$/CH$_3$OH) indicates quantitative conversion of the phosphine (R$_f$=0.81) to the rhodium complex (R$_f$=0.43). The solvent is removed under vacuum, the residue is taken up in 6 ml of methanol, and 150 ml of ether are added to the suspension. After stirring for 15 min under argon, the solid is filtered off with suction washed with ether and dried under high vacuum to give 1.35 g (1.48 mmol, 97% of theory) of an orange-yellow powder.

$^1$H NMR (CD$_2$Cl$_2$):very complex reproducible spectrum.

$^{31}$P NMR (CD$_2$Cl$_2$, against 85% H$_3$PO$_4$ as external standard):δ=32.8 ppm (d, J$_{Rh,P}$=150.3 Hz, width at half height approx. 30 Hz).

d) (3R,4R)(+)-1-Phenylaminocarbonyl-3,4-bis(diphenylphosphino)pyrrolidine (formula 31)

d$_1$) (3R,4R)(+)-3,4-Bis(diphenylphosphino)pyrrolidinium chloride

This is prepared analogously to b$_3$). Yield 74% of theory, m.p. 207°-209° C., $[\alpha]_D^{25}$=+163° (c=3.0 in 99% ethanol).

$^1$H NMR (CDCl$_3$):δ=9-11 (very broad s, 2H, NH$_2$+), 7.1-7.6 (m, 20H, arom. H), 3.62 (m, 2H, NCH$_2$), 3.16 (m, 2H, NCH$_2$), 2.95 (m, 2H, CHPPh$_2$) ppm.

d$_2$) (3R,4R)(+)-3,4-Bis(diphenylphosphino)pyrrolidine

This is prepared from d$_1$) analogously to c$_1$). The crude product melts at 120°-122° C.

$^1$H NMR (CD$_3$OD):δ=7.1-7.5 (m, 20H, arom. H), 4.82 (s, 1H, NH), 3.30-3.45 (m, 2H, CHPPh$_2$), 2.75-2.93 (m, 4H, CH$_2$) ppm.

d$_3$) (3R,4R)(+)-1-Phenylaminocarbonyl-3,4-bis(diphenylphosphino)pyrrolidine This is prepared from the crude product d$_2$) analogously to c$_2$). Yield:100%, m.p. 165°-167° C., TLC (cyclohexane/ethyl acetate 3:2):R$_f$=0.48.

$^1$H NMR (DMSO-d$_6$):δ=8.20 (s, 1H, NH), 7.05-7.50 (m, 24H, arom. H), 6.90 (m, 1H, arom. H), 3.90 (m, 2H, NCH$_2$), 3.43 (t, 2H, NCH$_2$), 2.92 (t, 2H, CHPPh$_2$) ppm.

d$_4$) [(3R,4R)(+)-1-Phenylaminocarbonyl-3,4-bis(diphenylphosphino)pyrrolidine-P,P'](1,5-cyclooctadiene)rhodium tetrafluoroborate This is prepared from the product d$_3$) analogously to c$_3$). Yellow-orange powder. Yield:91% of theory.

MS (FAB, 3-NBA): m/e=769 (molecular peak of the cation).

$^1$H NMR (CD$_2$Cl$_2$):δ=7.98 (m, 4H, arom. H), 7.52-7.80 (m, 12H, arom. H), 7.45 (m, 4H, arom. H), 7.31 (dd, 2H, arom. H), 7.15 (t, 2H, arom. H), 6.91 (m, approximate t, 1H, arom. H), 6.64 (s, 1H, NH), 5.20 (broad s, 2H, olef. H), 4.56 (qua, 2H, olef. H), 3.75 (m, 2H, NCH$_2$), 3.14 (m, 2H, NCH$_2$), 2.99 (m, 2H, CHPPh$_2$), 2.30-2.65 (m, 4H, allyl H of COD), 2.05-2.30 (m, 4H, allyl H of COD) ppm.

$^{31}$P NMR (CD$_2$Cl$_2$, against 85% H$_3$PO$_4$ as external standard):δ=34.1 ppm (d, J$_{Rh,P}$=149.0 Hz, width at half height approx. 30 Hz).

EXAMPLE 6

Preparation of Ruthenium Complexes of Chiral Diphosphines Which Are Known in Principle in the Literature e) [((S)-BINAP-P,P')(μ-iodo)(η-p-cymene)]ruthenium-(II) iodide (formula 16 where Y$^1$=Y$^{1(2)}$=I, R$^7$=CH$_3$, R$^8$=i-Pr, diphosphine ligand=(S)(−)-BINAP of formula 33)

The complex is prepared according to the principles given by K. Mashima et al., J. Chem. Soc., 1208 (1989) (no experimental data provided).

e₁) di-μ-iodo-diiodo-bis[(p-cymene)ruthenium(II)] alternative name:[(p-cymene)ruthenium(II) iodide] dimer A suspension of 5.23 g (20.0 mmol) of ruthenium(III) chloride trihydrate (Riedel-de Haen) and 10.90 g (80.0 mmol) of (R)(−)-5-isopropyl-2-methyl-1,3-cyclohexadiene (Merck-Schuchardt, alternative names:(R)(−)-α-phellandrene; p-mentha-1,5-diene) in 100 ml of 90% ethanol is heated at 50° C. for 5 hours under argon, the black suspension becoming an orange-colored solution. The solution is added dropwise over 30 min to a solution of 16.6 g (100.0 mmol) of potassium iodide in 70 ml of 50% ethanol. After one hour, the air-stable solid which has precipitated out is filtered off with suction on a sintered glass filter, washed with 50% ethanol and dried for a short time under high vacuum to give 6.7 g (6.85 mmol, 68% of theory) of a purple-colored powder, m.p. 226°-229° C. (with decomposition).

¹H NMR (DMSO-d₆):δ=5.87 (AB system, 8H, arom. H), 3.15 (sept, 2H, C$\underline{H}$(CH₃)₂), 2.39 (s, 6H, CH₃), 1.21 (d, 12H, CH(C$\underline{H}$₃)₂) ppm.

MS (FAB): cluster of isotope signals for (M-I)⁺=C₂₀H₂₈I₃Ru₂: m/e=858 (int. 4%), 857 (20%), 856 (15%), 855 (73%), 854 (55%), 853 (100%), 852 (99%), 851 (78%), 850 (77%), 849 (56%), 848 (24%), 847 (30%), 846 (12%), 845 (9%), 844 (7%). The intensity distribution of the isotope peaks was identical to a computer simulation for the above empirical formula.

e₂) [((S)(−)-BINAP-P,P')(μ-iodo)(η-p-cymene)]ruthenium(II) iodide 20 ml of a degassed ethanol/methylene chloride mixture (4:1) are added under argon to a mixture of 157 mg (0.16 mmol) of the product of e₁) and 200 mg (0.32 mmol) of (S)(−)-BINAP (Aldrich). Methylene chloride (approx. 3 ml) is then added dropwise until the solid has completely dissolved. The solution is stirred for 1 hour at 45° C. TLC (CH₂Cl₂/EtOAc 1:1) indicates complete conversion of the BINAP ($R_f$=0.79) and the complex of e₁) ($R_f$=0.58) to the product ($R_f$=0.35). The solvent is removed under vacuum and the residual solid is extracted with 30 ml of ethanol/methylene chloride (4:1). Undissolved solid is filtered off and the filtrate is concentrated under vacuum. n-Hexane is added dropwise until a marked turbidity appears. The mixture is left to crystallize for 12 hours at 0° C. and the crystals are filtered off with suction, washed with n-hexane and dried for a short time under high vacuum to give 270 mg (0.24 mmol, 75% of theory) of a brown powder, m.p. 225°-227° C. (with decomposition).

IR (KBr): 3050 (weak), 1433 (strong), 742 (strong), 697 (strong) cm⁻¹.

³¹P NMR (CDCl₃, against 85% H₃PO₄ as external standard):δ=41.6 ppm (P, d, $J_{P,P'}$=60.0 Hz), 24.7 ppm (P', d, $J_{P,P'}$=60.0 Hz).

f) [(S)-BINAP]ruthenium(II) dialkanoate complexes of formula 19 are prepared according to the instructions given by T. Ohta, H. Takaya, R. Noyori, Inorg. Chem., 27, 566 (1988), and by M. T. Ashby, J. Halpern, J. Am. Chem. Soc., 113, 589 (1991).

g) Ruthenium complexes of formula 18 are prepared according to the instructions given by H. Kawano et al., J. Chem. Soc. Perkin Trans. I, 1571 (1989).

What is claimed is:

1. A process for the preparation of 2(R)-benzylsuccinic acid derivatives of formula (1):

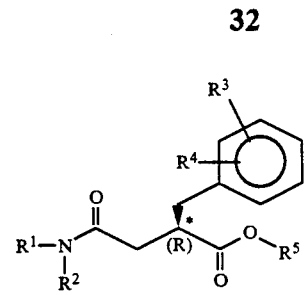

in which
R¹ and R²
a) are identical or different and are linear or branched alkyl having 1 to 7 carbon atoms or cycloalkyl having 5 to 7 carbon atoms, it being possible for said alkyl or cycloalkyl to be substituted by up to three identical or different radicals selected from the group consisting of
(C₁-C₇)-alkyl,
protected or unprotected hydroxyl,
(C₁-C₇)-alkoxy,
protected or unprotected amino,
protected or unprotected (C₁-C₇)-alkylamino, and
di-(C₁-C₇)-alkylamino, or
R¹ and R² can be bonded together to form a 5- to 7-membered ring of which 0, 1 or 2 ring members are identical or different and are oxygen or nitrogen atoms, it being possible for the ring to be unsubstituted or substituted by the aforementioned radicals, or
b) are phenyl groups which can be unsubstituted or substituted by groups having the meanings given below for R³ and R⁴,
R³ and R⁴ are identical or different and are hydrogen, trifluoromethyl, halogen or one of the substituents defined for R¹ and R² under a), and
R⁵ is a hydrogen atom,
which process comprises the steps
a) eliminating water from a phenylitaconic acid derivative of formula (4):

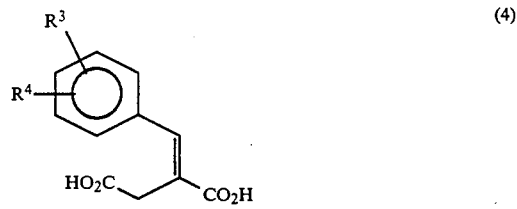

to form the anhydride of formula (7):

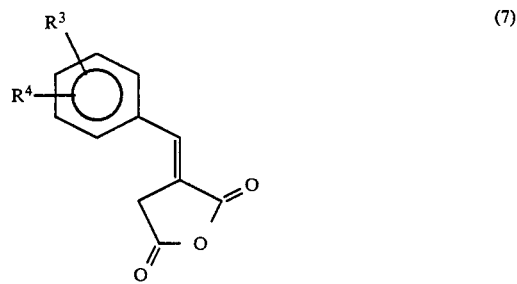

R³ and R⁴ being as defined above, b) reacting said anhydride of formula (7) with an amine of the formula

R¹R²NH,

R¹ and R² being defined above,
in a regioselective reaction to give the monoamide of formula (8):

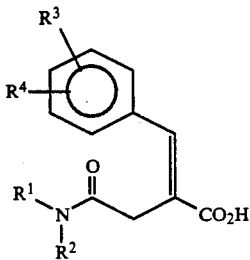

(8)

R¹, R², R³ and R⁴ being as defined above, and c) asymmetrically hydrogenating this monoamide of formula (8) in the presence of a rhodium(I) or ruthenium(II) diphosphine catalyst to give the 2(R)-benzylsuccinic acid derivative of formula (1).

2. A process as claimed in claim 1 wherein a compound of formula (1) is prepared in which the symbols have the following meanings:

—NR¹R² is selected from the group consisting of
pyrrolidinyl,
pyrazolidinyl,
imidazolidinyl,
piperidinyl,
piperazinyl,
tetrahydropyrimidinyl,
3-hydroxypiperidinyl,
4-hydroxypiperidinyl,
3-aminopiperidinyl,
4-aminopiperidinyl,
morpholinyl and
1,4-diazacycloheptyl,
it being possible for all the hydroxyl and amino groups to be protected or unprotected, and
R³, R⁴ and R⁵ are hydrogen.

3. A process as claimed in claim 1 wherein in step a) water is eliminated from the phenylitaconic acid derivative of formula (4) by converting said derivative to the anhydride of formula (7) in an ether in the presence of an excess of acetic anhydride.

4. A process as claimed in claim 3 wherein the ether is tetrahydrofuran and the reaction is carried out at room temperature.

5. A process as claimed in claim 1 wherein in step b) the amine of the formula

R¹R²NH is added in portions to a suspension of the anhydride of formula (7) in an inert solvent at a temperature of from −40° C. to +100° C.

6. A process as claimed in claim 1 wherein in step b) the amine of the formula

R¹R²NH is added in portions to a suspension of the anhydride of formula (7) in ethyl acetate at a temperature of from 0° to 30° C. over a time from 4 hours to 2 days.

7. The process as claimed in claim 1 wherein in step c) the catalyst is a rhodium(I) diphosphine catalyst.

* * * * *